(12) United States Patent
Rubinsky et al.

(10) Patent No.: US 8,298,222 B2
(45) Date of Patent: Oct. 30, 2012

(54) ELECTROPORATION TO DELIVER CHEMOTHERAPEUTICS AND ENHANCE TUMOR REGRESSION

(75) Inventors: Boris Rubinsky, Givataaim (IL); Jon Edd, Berkeley, CA (US); Liana Horowitz, Givataaim (IL)

(73) Assignee: The Regents of the University of California, Oakland, CA (US)

( * ) Notice: Subject to any disclaimer, the term of this patent is extended or adjusted under 35 U.S.C. 154(b) by 404 days.

(21) Appl. No.: 12/430,336

(22) Filed: Apr. 27, 2009

(65) Prior Publication Data
US 2009/0326436 A1    Dec. 31, 2009

Related U.S. Application Data

(63) Continuation-in-part of application No. 11/022,310, filed on Dec. 21, 2004, now abandoned.

(60) Provisional application No. 60/532,588, filed on Dec. 24, 2003.

(51) Int. Cl.
A61B 18/10    (2006.01)
(52) U.S. Cl. .......................................... 606/32
(58) Field of Classification Search .............. 606/32–50; 600/547; 604/20; 607/115–116
See application file for complete search history.

(56) References Cited

U.S. PATENT DOCUMENTS

| | | | |
|---|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |
| 4,810,963 A | 3/1989 | Blake-Coleman et al. |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |

(Continued)

FOREIGN PATENT DOCUMENTS

DE        863111        1/1953

(Continued)

OTHER PUBLICATIONS

Amash et al, "Quantitative assessment of impedance tomography for temperature measurement in microwave hyperthermia", 1988, Clin. Phys. Physiol. Meas., vol. 9, 49-53.*

(Continued)

*Primary Examiner* — Michael Peffley
*Assistant Examiner* — Ronald Hupczey, Jr.
(74) *Attorney, Agent, or Firm* — Karl Bozicevic; Bozicevic, Field & Francis LLP

(57) ABSTRACT

A method is disclosed for disrupting capillary blood flow and trapping materials such as chemotherapeutic agents in undesirable tissue, including cells of a cancerous or non-cancerous tumor. The method involves the placement of electrodes into or near the vicinity of capillary vessels supplying blood to capillaries in the undesirable tissue, and application of electrical pulses causing capillary blood flow disruption. In some cases, the electric pulses irreversibly permeate the cell membranes, thereby invoking cell death. The irreversibly permeabilized cells are left in situ and are removed by the body's immune system. The process may further comprise monitoring blood flow and/or infusion of a material such as a chemotherapeutic agent or marker into the blood.

18 Claims, 14 Drawing Sheets

U.S. PATENT DOCUMENTS

| | | | |
|---|---|---|---|
| 5,273,525 A | 12/1993 | Hofmann | |
| 5,283,194 A | 2/1994 | Schmukler | |
| 5,318,563 A | 6/1994 | Malis et al. | |
| 5,328,451 A | 7/1994 | Davis et al. | |
| 5,389,069 A | 2/1995 | Weaver | |
| 5,403,311 A | 4/1995 | Abele et al. | |
| 5,425,752 A | 6/1995 | Vu'Nguyen | |
| 5,439,440 A | 8/1995 | Hofmann | |
| 5,458,625 A | 10/1995 | Kendall | |
| 5,533,999 A | 7/1996 | Hood et al. | |
| 5,536,240 A | 7/1996 | Edwards et al. | |
| 5,575,811 A | 11/1996 | Reid et al. | |
| 5,626,146 A | 5/1997 | Barber et al. | |
| 5,634,899 A | 6/1997 | Shapland et al. | |
| 5,674,267 A | 10/1997 | Mir et al. | |
| 5,702,359 A | 12/1997 | Hofmann | |
| 5,718,246 A | 2/1998 | Vona | |
| 5,720,921 A | 2/1998 | Meserol | |
| 5,778,894 A | 7/1998 | Dorogi et al. | |
| 5,782,882 A | 7/1998 | Lerman et al. | |
| 5,800,378 A | 9/1998 | Edwards et al. | |
| 5,810,762 A | 9/1998 | Hofmann | |
| 5,836,905 A | 11/1998 | Lemelson et al. | |
| 5,843,026 A | 12/1998 | Edwards et al. | |
| 5,873,849 A | 2/1999 | Bernard | |
| 5,919,142 A | 7/1999 | Boone et al. | |
| 5,947,889 A | 9/1999 | Hehrlein | |
| 5,983,131 A | 11/1999 | Weaver et al. | |
| 5,991,697 A | 11/1999 | Nelson et al. | |
| 5,999,847 A | 12/1999 | Elstrom | |
| 6,009,347 A | 12/1999 | Hofmann | |
| 6,010,613 A * | 1/2000 | Walters et al. | 205/701 |
| 6,016,452 A | 1/2000 | Kasevich | |
| 6,041,252 A | 3/2000 | Walker et al. | |
| 6,055,453 A | 4/2000 | Hofmann et al. | |
| 6,068,650 A | 5/2000 | Nanda et al. | |
| 6,085,115 A | 7/2000 | Weaver et al. | |
| 6,090,106 A | 7/2000 | Goble et al. | |
| 6,102,885 A | 8/2000 | Bass | |
| 6,106,521 A | 8/2000 | Blewett et al. | |
| 6,109,270 A | 8/2000 | Mah et al. | |
| 6,122,599 A | 9/2000 | Mehta | |
| 6,132,419 A | 10/2000 | Hofmann | |
| 6,159,163 A | 12/2000 | Strauss et al. | |
| 6,208,893 B1 | 3/2001 | Hofmann | |
| 6,210,402 B1 | 4/2001 | Olsen et al. | |
| 6,212,433 B1 | 4/2001 | Behl | |
| 6,216,034 B1 | 4/2001 | Hofmann | |
| 6,219,577 B1 | 4/2001 | Brown et al. | |
| 6,241,702 B1 | 6/2001 | Lundquist et al. | |
| 6,261,831 B1 | 7/2001 | Agee | |
| 6,278,895 B1 * | 8/2001 | Bernard | 604/20 |
| 6,300,108 B1 | 10/2001 | Rubinsky | |
| 6,326,177 B1 | 12/2001 | Schoenbach et al. | |
| 6,347,247 B1 | 2/2002 | Dev et al. | |
| 6,349,233 B1 | 2/2002 | Adams | |
| 6,351,674 B2 | 2/2002 | Silverstone | |
| 6,387,671 B1 * | 5/2002 | Rubinsky et al. | 435/173.7 |
| 6,403,348 B1 | 6/2002 | Rubinsky et al. | |
| 6,470,211 B1 | 10/2002 | Ideker et al. | |
| 6,482,619 B1 | 11/2002 | Rubinsky et al. | |
| 6,493,592 B1 | 12/2002 | Leonard et al. | |
| 6,500,173 B2 | 12/2002 | Underwood et al. | |
| 6,526,320 B2 | 2/2003 | Mitchell | |
| 6,562,604 B2 | 5/2003 | Rubinsky et al. | |
| 6,607,529 B1 | 8/2003 | Jones et al. | |
| 6,611,706 B2 | 8/2003 | Avrahami et al. | |
| 6,613,211 B1 | 9/2003 | McCormick et al. | |
| 6,627,421 B1 | 9/2003 | Unger et al. | |
| 6,653,091 B1 | 11/2003 | Dunn et al. | |
| 6,669,691 B1 | 12/2003 | Taimisto | |
| 6,692,493 B2 | 2/2004 | McGovern et al. | |
| 6,697,669 B2 | 2/2004 | Dev et al. | |
| 6,697,670 B2 | 2/2004 | Chornenky et al. | |
| 6,702,808 B1 | 3/2004 | Kreindel | |
| 6,795,728 B2 | 9/2004 | Chornenky et al. | |
| 6,801,804 B2 | 10/2004 | Miller et al. | |
| 6,865,416 B2 | 3/2005 | Dev et al. | |
| 6,892,099 B2 | 5/2005 | Jaafar et al. | |
| 6,912,417 B1 | 6/2005 | Bernard et al. | |
| 6,927,049 B2 | 8/2005 | Rubinsky et al. | |
| 6,962,587 B2 | 11/2005 | Johnson et al. | |
| 6,972,014 B2 | 12/2005 | Eum et al. | |
| 6,994,706 B2 | 2/2006 | Chornenky et al. | |
| 7,053,063 B2 | 5/2006 | Rubinsky et al. | |
| 7,063,698 B2 | 6/2006 | Whayne et al. | |
| 7,130,697 B2 | 10/2006 | Chornenky et al. | |
| 7,211,083 B2 | 5/2007 | Chornenky et al. | |
| 7,267,676 B2 | 9/2007 | Chornenky et al. | |
| 2001/0044596 A1 | 11/2001 | Jaafar | |
| 2002/0010491 A1 | 1/2002 | Schoenbach | |
| 2002/0055731 A1 | 5/2002 | Atala et al. | |
| 2002/0077676 A1 | 6/2002 | Schroeppel et al. | |
| 2002/0099323 A1 | 7/2002 | Dev et al. | |
| 2002/0133324 A1 | 9/2002 | Weaver et al. | |
| 2002/0138117 A1 | 9/2002 | Son | |
| 2002/0193831 A1 | 12/2002 | Smith, III | |
| 2003/0009110 A1 | 1/2003 | Tu et al. | |
| 2003/0060856 A1 | 3/2003 | Chornenky et al. | |
| 2003/0088189 A1 | 5/2003 | Tu et al. | |
| 2003/0130711 A1 | 7/2003 | Pearson et al. | |
| 2003/0170898 A1 | 9/2003 | Gundersen et al. | |
| 2003/0199050 A1 | 10/2003 | Mangano et al. | |
| 2003/0208200 A1 | 11/2003 | Palanker et al. | |
| 2003/0225360 A1 | 12/2003 | Eppstein et al. | |
| 2004/0019371 A1 | 1/2004 | Jaafar et al. | |
| 2004/0059389 A1 | 3/2004 | Chornenky et al. | |
| 2004/0146877 A1 | 7/2004 | Diss et al. | |
| 2004/0153057 A1 | 8/2004 | Davison | |
| 2004/0243107 A1 | 12/2004 | Mackoviak | |
| 2004/0267189 A1 | 12/2004 | Mavor et al. | |
| 2005/0043726 A1 | 2/2005 | McHale et al. | |
| 2005/0049541 A1 | 3/2005 | Behar et al. | |
| 2005/0165393 A1 | 7/2005 | Eppstein | |
| 2005/0171523 A1 | 8/2005 | Rubinsky et al. | |
| 2005/0171574 A1 | 8/2005 | Rubinsky et al. | |
| 2005/0182462 A1 | 8/2005 | Chornenky et al. | |
| 2005/0261672 A1 | 11/2005 | Deem et al. | |
| 2005/0288730 A1 | 12/2005 | Deem et al. | |
| 2006/0015147 A1 | 1/2006 | Persson et al. | |
| 2006/0025760 A1 * | 2/2006 | Podhajsky | 606/38 |
| 2006/0079883 A1 | 4/2006 | Elmouelhi et al. | |
| 2006/0121610 A1 | 6/2006 | Rubinsky et al. | |
| 2006/0212078 A1 | 9/2006 | Demarais et al. | |
| 2006/0217703 A1 | 9/2006 | Chornenky et al. | |
| 2006/0264752 A1 | 11/2006 | Rubinsky et al. | |
| 2007/0043345 A1 | 2/2007 | Davalos et al. | |
| 2007/0118069 A1 | 5/2007 | Persson et al. | |
| 2008/0052786 A1 | 2/2008 | Lin et al. | |

FOREIGN PATENT DOCUMENTS

| | | |
|---|---|---|
| DE | 4000893 | 7/1991 |
| EP | 0378132 | 7/1990 |
| EP | 0935482 | 5/2005 |
| WO | 96/39531 | 12/1996 |
| WO | 9639531 | 12/1996 |
| WO | 00/20554 | 4/2000 |
| WO | 0020554 | 4/2000 |
| WO | 01/07583 | 2/2001 |
| WO | 01/07584 | 2/2001 |
| WO | 01/07585 | 2/2001 |
| WO | 01/10319 | 2/2001 |
| WO | 0107583 | 2/2001 |
| WO | 0107584 | 2/2001 |
| WO | 0107585 | 2/2001 |
| WO | WO 01/07583 | 2/2001 |
| WO | 01/81533 | 11/2001 |
| WO | 0181533 | 11/2001 |
| WO | 02/078527 | 10/2002 |
| WO | WO 02/078527 | 10/2002 |
| WO | 02/089686 | 11/2002 |
| WO | 02/100459 | 12/2002 |
| WO | 03/047684 | 6/2003 |
| WO | 03/099382 | 12/2003 |
| WO | 2004/037341 | 5/2004 |
| WO | 2004037341 | 5/2004 |

OTHER PUBLICATIONS

Brown et al, "Blood Flow imaging using electrical impedance tomography", 1992, Clin. Phys. Physiol. Meas., vol. 13, 175-179.*
Sersa et al, "Tumor blood flow modifying effects of electrochemotherpay: a potential vascular target mechanism", 2003, Radiologic Oncology, 37(1), 43-48.*
Mir et al, "Mechanisms of electrochemotherapy", 1999, Advanced Drug Delivery Reviews, 35, 107-118.*
Davalos et al., "A Feasibility Study for Electrical Impedance Tomography as a Means to Monitor Tissue Electroporation for Molecular Medicine" IEEE Transactions on Biomedical Engineering, 49(4):400-403 (Apr. 2002).
Barber, Electrical Impedance Tomography Applied Potential Tomography, Advances in Biomedical Engineering, Beneken and Thevenin, eds., IOS Press, 1993.
Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211-215, vol. I, Piscataway, NJ, USA.
Beneken and Thevenia (eds) IOS Press pp. 165-173 (1993).
Cook, et al., ACT3: A High-Speed, High-Precision Electrical Impedance Tomograph, *IEEE Transactions on Biomedical Engineering*, vol. 41, No. 8, Aug. 1994.
Davalos, et al., Tissue Ablation with Irreversible Electroporation, *Annals of Biomedical Engineering*, vol. 33, No. 2, Feb. 2005.
Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.
Erez, et al., Controlled Destruction and Temperature Distributions in Biological Tissues Subjected to Monoactive Electrocoagulation, *Transactions of the ASME: Journal of Mechanical Design*, vol. 102, Feb. 1980.
Gençer, et al., Electrical Impedance Tomography: Induced-Current Imaging Achieved with a Multiple Coil System, *IEEE Transactions on Biomedical Engineering*, vol. 43, No. 2, Feb. 1996.
Griffiths, Tissue Spectroscopy with Electrical Impedance Tomography: Computer Simulations, *IEEE Transactions on Biomedical Engineering*, vol. 42, No. 9, Sep. 1995.
Lurquin, Gene Transfer by Electroporation, *Molecular Biotechnology*, vol. 7, 1997.
Thompson, et al., To determine whether the temperature of 2% lignocaine gel affects the initial discomfort which may be associated with its instillation into the male urethra, *BJU International* (1999), 84, 1035-1037.
Amasha, et al., Quantitative Assessment of Impedance Tomography for Temperature Measurements in Microwave Hyperthermia, *Clin. Phys. Physiol. Meas.*, 1998, Suppl. A, 49-53.
Andreason, Electroporation as a Technique for the Transfer of Macromolecules into Mammalian Cell Lines, *J. Tiss. Cult. Meth.*, 15:56-62, 1993.
Baker, et al., Calcium-Dependent Exocytosis in Bovine Adrenal Medullary Cells with Leaky Plasma Membranes, *Nature*, vol. 276, pp. 620-622, 1978.
Barber, Electrical Impedance Tomography Applied Potential Tomography, Advances in Biomedical Engineering, Beneken and Thevenin, eds., IOS Press, 1993, pp. 165-173.
Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat No. 01CH37251). IEEE, Part vol. 1, 2001, pp. 211-215, vol. I, Piscataway, NJ, USA.
Blad, et al., Impedance Spectra of Tumour Tissue in Comparison with Normal Tissue; a Possible Clinical Application for Electrical Impedance Tomography, *Physiol. Meas.* 17 (1996) A105-A115.
Bown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.
Brown, et al., Blood Flow Imaging Using Electrical Impedance Tomography, *Clin. Phys. Physiol. Meas.*, 1992, vol. 13, Suppl. A, 175-179.
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W.,et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, *IEEE Transactions on Biomedical Engineering*, vol. 41, No. 8, pp. 713-722, Aug. 1994.
Cowley, Good News for Boomers, *Newsweek*, Dec. 30, 1996/Jan. 6, 1997.
Cox, et al., Surgical Treatment of Atrial Fibrillation: A Review, *Europace* (2004) 5, S20-S-29.
Crowley, Electrical Breakdown of Biomolecular Lipid Membranes as an Electromechanical Instability, *Biophysical Journal*, vol. 13, pp. 711-724, 1973.
Davalos, et al., Tissue Ablation with Irreversible Electroporation, *Annals of Biomedical Engineering*, vol. 33, No. 2, pp. 223-231, Feb. 2005.
Davalos, et al., Theoretical Analysis of the Thermal Effects During In Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, *IEEE Transactions on Biomedical Engineering*, vol. 49, No. 4, pp. 400-403, Apr. 2002.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, *Am J. Physiol Cell Physiol* 289: 233-245, 2005.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.
Dev, et al., Medical Applications of Electroporation, *IEEE Transactions of Plasma Science*, vol. 28, No. 1, pp. 206-223, Feb. 2000.
Duraiswami, et al., Boundary Element Techniques for Efficient 2-D and 3-D Electrical Impedance Tomography, *Chemical Engineering Science*, vol. 52, No. 13, pp. 2185-2196, 1997.
Duraiswami, et al., Efficient 2D and 3D Electrical Impedance Tomography Using Dual Reciprocity Boundary Element Techniques, *Engineering Analysis with Boundary Elements* 22, (1998) 13-31.
Duraiswami, et al., Solution of Electrical Impedance Tomography Equations Using Boundary Element Methods, *Boundary Element Technology* XII, 1997, pp. 226-237.
Edd, J., et al., In-Vivo Results of a New Focal Tissue Ablation Technique: Irreversible Electroporaton, *IEEE Trans. Biomed. Eng.* 53 (2006) p. 1409-1415.
Erez, et al., Controlled Destruction and Temperature Distributions in Biological Tissues Subjected to Monoactive Electrocoagulation, *Transactions of the ASME: Journal of Mechanical Design*, vol. 102, pp. 42-49, Feb. 1980.
Foster, R.S., et al., High-intensity focused ultrasound in the treatment of prostatic disease. *Eur. Urol.*, 1993. 23: 44-7).
Fox, et al., Sampling Conductivity Images via MCMC, Mathematics Department, Auckland University, New Zealand, May 1997.
Gauger, et al., A Study of Dielectric Membrane Breakdown in the Fucus Egg, *J. Membrane Biol.*, vol. 48, No. 3, pp. 249-264, 1979.
Gehl, et al., In Vivo Electroporation of Skeletal Muscle: Threshold, Efficacy and Relation to Electric Field Distribution, *Biochimica et Biphysica Acta* 1428, 1999, pp. 233-240.
Gençer, et al., Electrical Impedance Tomography: Induced-Current Imaging Achieved with a Multiple Coil System, *IEEE Transactions on Biomedical Engineering*, vol. 43, No. 2, pp. 139-149, Feb. 1996.
Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, pp. 948-954, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, pp. 5-35, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed.* Eng. vol. 2 2000. 157-187.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

\* cited by examiner

BACKGROUND

ELECTROPORATION TO DELIVER CHEMOTHERAPEUTICS AND ENHANCE TUMOR REGRESSION

CROSS-REFERENCE

This application is a continuation-in-part of U.S. application Ser. No. 11/022,310 filed Dec. 21, 2004 (now abandoned) which application claims the benefit of U.S. Provisional Application No. 60/532,588, filed Dec. 24, 2003, both of which applications are incorporated herein by reference noting that this application controls with regard to any conflicts with the earlier filings.

FIELD OF THE INVENTION

This invention relates to the field of electrode devices useful to disrupt blood flow in order to carry out treatments.

BACKGROUND OF THE INVENTION

Cancer is second only to heart disease as a cause of death, accounting for 22% of all deaths (Fraumeni J. et al. Epidemiology of cancer. In: Cancer—principles and practice of oncology, DeVita V., et al., (eds.) pp. 150, Lippincott J. R. Co., Philadelphia, 1993. Colon cancer, melanoma and breast cancer are three particularly problematic types of cancer.

Melanomas are aggressive, frequently metastatic tumors derived from either melanocytes or melanocyte-related nevus cells ("Cellular and Molecular Immunology" (1991) (eds) Abbas A. K., W.B. Saunders Company, Philadelphia: pages 340-341) which make up approximately 3% of all skin cancers. Of particular concern is the current worldwide increase in melanoma which is unsurpassed by any other neoplasm with the exception of lung cancer in women ("Cellular and Molecular Immunology" (1991) (eds) Abbas, A. K., et al., W.B. Saunders Company Philadelphia pages: 340-342; Kirkwood and Agarwala (1993) Principles and Practice of Oncology 7:1-16). The aggressiveness of melanoma is such that even when melanoma is apparently localized to the skin, up to 30% of the patients will develop systemic metastasis and the majority will die.

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

Colon cancer is the second most frequently diagnosed malignancy in the United States, as well as the second most common cause of cancer death. About 100,000 new cases of colon cancer are diagnosed yearly, with about 50,000 deaths. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases. Recurrence following surgery (the most common form of therapy) is a major problem and is often the ultimate cause of death. In spite of considerable research into therapies for the disease, colon cancer remains difficult to diagnose and treat.

While metastatic primary tumors can in many cases be surgically removed, metastases, such as disseminated micrometastases, can be difficult or impossible to locate and/or reach and thus surgical removal of such metastases is usually not an option. Therefore, prevention of metastasis is necessary to improve the prognosis of cancer patients.

In order to treat cancer effectively, efficient removal of the primary tumor mass, prevention of secondary tumor growth, and eradication of metastatic cells must be achieved. Surgical excision of tumors is the most widely employed therapeutic modality for the treatment of cancer, in which the primary goal is the complete eradication of local and regional tumor. This involves removal of adequate margins of normal tissue surrounding the tumor, and radical wide excision in order to prevent local recurrence. However, despite major advances in the surgical pre- and postoperative care of patients, surgical treatment of malignant neoplasms remains highly limited (Eilber, F. R., Principles of cancer surgery. In: Cancer Treatment, Haskell C M, (ed.) 5th ed., pp. 47, W.B. Saunders Co. Philadelphia, 2001). Surgical techniques are effective only in the area of the primary tumor or regional lymphatics and do not affect neoplasms located outside the operative field. Furthermore, due to anatomic location, many tumors cannot be treated by surgical resection because removal of an adequate margin of normal tissue cannot be achieved. Also, surgical treatment is often not an option for tumors intimately involving major blood vessels or essential organs. As well, many patient present problematic medical histories, such as cerebrovascular or cardiovascular accidents, or uncontrolled diabetes, rendering them poor surgical candidates because of their high postoperative mortality rate. Also, in many cases, tumor excision can not be performed without causing unacceptable levels of impairment of physiologic functions or cosmetic damage.

Chemotherapy alone or in combination with surgery is commonly the most efficient anti-cancer remedy (Haskell, C. M., Principles of cancer chemotherapy. In: Cancer Treatment (ed.) 5th ed. pp. 62-86, W.B. Saunders Co. Philadelphia, 2001). However, chemotherapeutic agents often cause severe and unacceptable side-effects, such as bone marrow and lymphoid organ damage resulting in immunosuppression, thereby rendering subjects highly vulnerable to lethal opportunistic infections, as well as various other types of organ toxicities. Thus, the use of cytotoxic drugs is limited only to tolerated doses. One way to reduce minimal therapeutic doses of chemotherapeutic agents would be to enhance the efficiency of uptake of chemotherapeutic drugs into cancer cells.

During the last two decades, various techniques based on biological, chemical and physical processes have been developed for facilitating incorporation of macromolecules into cells. Methods for intracellular delivery of exogenous substances based on biological phenomena have employed molecules controlling the activity of specific membrane channels in various cell types (Heppel and Weisman, 1985. J Membr Biol. 86:189), pore-forming toxins (Ahnert-Higler et al., 1989. Methods Cell Biology 31:63) and liposome-endocytosis mediated delivery of compounds (Friend et al., 1996. Biophys Acta 1278:41). Some permeabilization methods are based on chemical modification of cell membranes by various substances, most commonly via the use of detergents as permeabilizing agents.

Electroporation, also known as electropermeabilization or electroinjection, is the permeabilization of cell membranes as a consequence of the application of certain short and intense electric fields across the cell membrane, the cells or the tissues. This may be 50-200 μs pulses of high-strength electric fields in the range of 500-5000 V/cm. Typically, a sequence of eight 100 μs pulses of approximately 1000 V/cm is applied.

The permeabilization can be temporary (reversible electroporation) or permanent (irreversible electroporation) as a function of the electrical field magnitude and duration, and the number of pulses.

Reversible Electroporation

Reversible electroporation, which involves the ability of the membrane to reseal, was discovered during the late 1970s (Kinosita Jr, K. and T. Y. Tsong, Hemolysis of human erythrocytes by a transient electric field. 1977. *Proc. Natl. Acad. Sci. USA*). Reversible electroporation is commonly used in vitro to facilitate the penetration of various otherwise nonpermeable macromolecules across the cell membrane. It can also be used to target the delivery and enhance the uptake of imaging agents, which are chemicals designed to allow clinicians to determine whether a mass is benign or malignant and locate metastatic cancer sites in the body.

Irreversible Electroporation

Irreversible electroporation is a phenomenon in which high electrical fields are delivered across cells in short, micro- to millisecond pulses. The pulses create irreversible defects (pores) in the cell membrane lipid bilayer, causing cell death through loss of cell homeostasis. Non Thermal Irreversible Electroporation ("NTIRE") causes irreversible electroporation effects without causing thermal damage.

Electrochemotherapy

Electrochemotherapy ("ECT") and supra-poration are minimally invasive tissue ablation techniques that employ reversible electroporation pulses to reversibly permeabilize the cell membrane and thereby facilitate the penetration into cells of small amounts of non-permeant or lowpermeant anticancer drugs, such as bleomycin or cisplatin. A major advantage of ECT is that the technique selectively kills, through the use of bleomycin, only the dividing tumor cells and spares the normal non-dividing cells.

The predominant underlying mechanism of electrochemotherapy is electroporation of cells in endothelial tissues, which facilitates access of poorly permeant and nonpermeant molecules, including cytotoxic drugs such as bleomycin ("BLM") and cisplatin, into vascular endothelial cells.

Cultured endothelial cells are susceptible to electrochemotherapy with BLM and to the same extent as tumor cells in the case of electrochemotherapy with cisplatin (Cemazar et al., 2001). Therefore, by electroporation of endothelial cells in tumor blood vessels, these may also become susceptible to chemotherapeutics, leading to endothelial cell death, vessel occlusion and abrogated tumor blood flow, thus inducing a cascade of cell death in the surroundings of the occluded blood vessel. As such, electrochemotherapy is a vascular disrupting therapy that causes a selective shutdown of established tumor vasculature and can lead to secondary tumor cell death (Tozer et al., 2001, 2005; Siemann et al, 2005).

Several prior art approaches employing electric fields have been employed to treat tumors. One approach has employed electroporation in conjunction with daunorubicin, doxorubicin, etoposide, paclitaxel, carboplatin or cisplatin in order to attempt to potentiate their cytotoxic effect against cultured cells (Gehl, J., et al., 1998. Anticancer Drugs 9:319).

Another approach has used very high strength electric field electroporation (1,300 V/cm) in conjunction with administration of bleomycin to attempt to treat head and neck squamous cell carcinoma (Belehradek, J. J., et al., 1993. Cancer 72:3694).

All of these prior art approaches suffer from significant disadvantages. For example, none has been shown to be effective in curing cancer at a metastatic stage. Thus, all prior art approaches have failed to provide an adequate solution for treating tumors using electrical fields.

Accordingly, there is a widely recognized need for, and it would be highly advantageous to have, a method and apparatus devoid of the above limitations.

The present inventors have found through histological analysis of electroporated tissue that in regions of tissue which are irreversibly electroporated, electrochemotherapy has a direct cytotoxic effect on tumor cells, as well as a vascular disrupting effect.

The applications of local blood flow cessation with non-thermal, irreversible electroporation and targeted delivery of chemotherapeutics, as well as use of reversible electroporation for targeted delivery of medical imaging agents are disclosed and described here.

SUMMARY OF THE INVENTION

The present inventors present a method by which tumor regression is enhanced by in vivo electroporation, which can be used to enhance the efficacy of chemotherapeutics. Techniques involving non-thermal irreversible electroporation are presented. Also presented is a method of decreasing blood flow in capillaries. Methods involving reversible electroporation are also discussed, which have applications in medical imaging.

An aspect of the invention is treating cancer by infusing a chemotherapeutic agent into blood, and applying current pulses of very precisely determined length and voltage. This in turn disrupts blood flow in capillaries and assists in trapping the chemotherapeutic agent in a target area (e.g., within endothelial cells of capillary walls that vascularize a tumor).

In certain aspects, the invention is a method of reducing the minimal therapeutic dose of chemotherapeutic agents by enhancing the efficiency of uptake of chemotherapeutic agents into cancer cells. Electroporation of cells in endothelial tissues facilitates access of poorly permeant and nonpermeant molecules, including chemotherapeutic drugs such as bleomycin ("BLM") and cisplatin, into vascular endothelial cells.

In other aspects, the invention is a method comprising the steps of infusing a higher than normal concentration of a chemotherapeutic agent into a blood vessel immediately upstream of a targeted area, such as a tumor, and applying current when the agent reaches capillaries at the targeted area to disrupt blood flow through the capillaries and trap the agent in the tumor.

In a specific embodiment, the invention is a method of treating cancer, whereby the method comprises the following steps:

(a) identifying a grouping of biological cells in a tissue of a living mammal as being cancer cells;

(b) infusing a chemotherapeutic agent into a vessel system of a bed of capillaries at the targeted area; and (c) applying current when the agent reaches the targeted area to disrupt blood flow in the capillaries and trap the chemotherapeutic agent at the targeted area.

In further embodiments, the method involves continuously detecting a ratio of electric current through the cells to voltage across the cells as an indication of degree of electroporation of the biological cells; and adjusting a determined magnitude of the applied voltage in accordance with changes in detected magnitude of the current-to-voltage ratio to achieve a disruption of blood flow in capillaries and permeation of the chemotherapeutic agent into capillary endothelial cells that vascularize the grouping of cells identified as being cancer cells at the target site.

In some aspects, the invention is a method of disrupting blood flow through capillaries and facilitating the permeation of an agent into a target area of tissue, comprising the steps of:

(a) identifying a target area of tissue of interest comprised of capillaries;

(b) placing a first electrode and a second electrode such that capillaries of the identified tissue of interest are positioned between the first and second electrodes;

(c) administering an agent;

(d) applying electrical pulses between the first and second electrodes in an amount sufficient to disrupt blood flow through the capillaries, trapping the agent in the capillaries and facilitating the permeation of the agent into cells of the target area of tissue of interest.

In some embodiments, the material is a chemotherapeutic agent or an agent readily detected by an imaging system or a combination of such agents.

In some embodiments, the target area of tissue is chosen from a cancerous tumor, a benign tumor, and a portion of an organ targeted for removal.

In some embodiments, the method further comprises allowing the cells of the target area deprived of blood flow to be removed by internal systems of an organism.

In further embodiments, the electrical pulses are applied for a duration and amount to avoid thermal damage, e.g. in a range of from about 5 microseconds to about 62 seconds.

In further embodiments, the electrical pulses are applied for a period of about 100 microseconds, ±about 10 microseconds.

In further embodiments, about 1 to about 15 pulses or larger numbers of pulses, e.g. up to 25, up to 50, up to 75, or up to 100 pulses, are applied.

In further embodiments, about eight pulses of about 100 microseconds each in duration are applied and other numbers of pulses and durations can be applied to obtain a desired result.

In further embodiments, the pulses produce a voltage gradient in a range of from about 50 volt/cm to about 8000 volt/cm.

Those skilled in the art will recognize that specific examples are provided herewith respect to the number of pulses, the length of each pulse, and the voltage provided in each pulse. Those skilled in the art will understand that these parameters can be varied over a considerable range in order to obtain the desired result which is to carry out irreversible electroporation in a limited area and disrupt blood flow in capillaries between the electrodes without raising the temperature of the tissue so as to cause thermal damage, e.g. keeping tissue temperature in the affected area below about 50° C.

In yet another embodiment, the first electrode is placed at about 5 mm to 10 cm from the second electrode with capillaries positioned between the electrodes.

In another embodiment, the first and second electrodes are positioned in an area of tissue of interest in capillaries upstream of the targeted area, in a direction of blood flow toward the targeted area of tissue.

In some aspects, the invention is a method of enhancing the delivery of an agent into a target area of tissue, comprising the steps of:

(a) identifying an area of tissue of interest comprised of capillaries;

(b) placing a first electrode and a second electrode such that capillaries of the identified tissue of interest are positioned between the first and second electrodes;

(c) administering an agent to a vessel at a point upstream of blood flow to the capillaries; and (d) applying electrical pulses between the first and second electrodes in an amount sufficient to disrupt blood flow through the capillaries, thereby trapping the agent in the capillaries and facilitating the permeation of the agent into cells of the area of tissue of interest.

In some embodiments, the material is an imaging agent readily detected by an imaging system.

It is noted that an electrical pulse can either have no effect on the cell membrane, effect internal cell components, reversibly open the cell membrane after which cells can survive, or irreversibly open the cell membrane. When the membrane of a cell is irreversibly opened the cell dies. When a sufficient number of cells in an area are killed (e.g. capillary cells) blood flow to that area through the capillaries is disrupted. When blood flow to other cells is disrupted those cells die. Others have generally considered irreversible electroporation of tissue to be undesirable due to the possibility of instantaneous necrosis of the entire tissue affected by the electrical field, regardless of its diseased or healthy state. Irreversible electroporation is detrimental in certain applications, such as gene therapy or electrochemotherapy, where the sole purpose of the electric pulses is to facilitate the introduction of the drug or gene into the cells of a tissue without killing the cell (Mir., L. M. and Orlowski, S., *The basis of electrochemotherapy*, in *Electrochemotherapy, electrogenetherapy, and transdermal drug delivery: Electrically mediated delivery of molecules to cells*, Jaroszeski, M. J., et al, Editors, 2000, Humana Press, p. 99-118).

In contrast, irreversible electroporation to disrupt blood flow in capillaries can provide useful treatments. The method is carried out using electrical pulses to serve as the active means for tissue destruction by a specific means, i.e. by fatally disrupting the cell membrane. Electrochemotherapy may be selective, but it does require the combination of chemical agents with the electrical field. Irreversible electroporation to disrupt blood flow in capillaries, although non-selective, may be used for the ablation of undesirable tissue (such as a tumor) as a minimally invasive surgical procedure with or without the use of adjuvant drugs. Its non-selective mode of tissue ablation is acceptable in the field of minimally invasive surgery and can provide results which in some ways are comparable to cryosurgery, non-selective chemical ablation and high temperature thermal ablation.

These and further features, advantages and objects of the invention will be better understood from the description that follows.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

In FIG. 2A electrodes 1 and 2 are shown respectively surrounded by irreversibly electroporated areas 3 and 3'. FIGS. 2B and 2C show electrodes 1 and 2 surrounded by irreversibly electroporated area 3.

FIGS. 3A, 3B and 3C show electrodes 1 and 2 surrounded by irreversibly electroporated area 3.

FIGS. 4A, 4B and 4C are schematic images showing the effect of electrode diameter for a 4-electrode configuration with 10 mm spacing wherein FIG. 4A is for 0.5 mm diameter and 940V; FIG. 4B is for 1.0 mm diameter and 1404V and FIG. 4C is for 1.5 mm and 1685V. FIGS. 4A, 4B and 4C show electrodes 1, 2, 4 and 5. FIG. 4A shows electrodes 1 and 2 surrounded by irreversibly electroporated areas 3 and 3' and electrodes 4 and 5 are surrounded respectively by irreversibly electroporated areas 6 and 6'.

FIG. 5A shows results with a 5 mm and 910V; FIG. 5B 7.5 mm and 1175V and FIG. 5C 10 mm and 1404V. FIGS. 5A, 5B and 5C show electrodes 1, 2, 4 and 5 surrounded by irreversibly electroporated area 3.

FIG. 6 shows electrodes 1 and 2 surrounded by irreversibly electroporated area 3 and further is surrounded by reversibly electroporated area 3' produced using the voltages shown above in connection with FIG. 6.

FIG. 7 is a schematic image showing reversible electroporation with 1 mm electrodes, 10mm spacing. A voltage of 189V applied between the electrodes induces reversible electroporation without any irreversible electroporation by not surpassing the 680V/cm irreversible electroporation threshold anyone in the domain. The shaded area is greater than 360 V/cm. FIG. 7 shows electrodes 1 and 2 surrounded by irreversibly electroporated areas 3 and 3'.

FIG. 8A no blood flow or metabolism. FIG. 8B wb=1 kg/m3, cb=3640 J/(kg K), Tb=37° C., and q'''=33.8 kW/m3. FIGS. 8A and 8B show electrodes 1 and 2 surrounded by irreversibly electroporated area 3.

FIG. 9 shows electrodes 1 and 2 with liver tissue 7 positioned therebetween.

FIG. 12 also shows conditions through a cross section of a liver slab through the center of the electroporated area. Height of the slab is 4 mm.

DETAILED DESCRIPTION OF THE INVENTION

Figure 1:
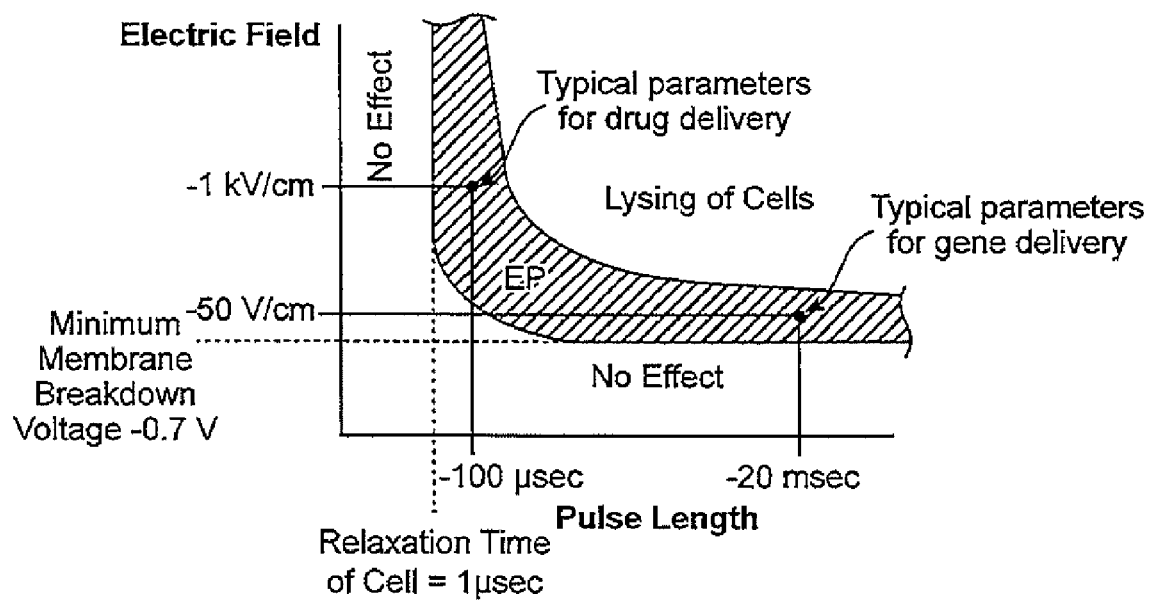
FIG. 1 is a graph showing a schematic relationship between field strength and pulselength applicable to the electroporation of cells.

Before the present methods, treatments and devices are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

It must be noted that as used herein and in the appended claims, the singular forms "a", "an", and "the" include plural referents unless the context clearly dictates otherwise. Thus, for example, reference to "a capillary" includes a plurality of such capillaries and reference to "the pulse" includes reference to one or more pulses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "reversible electroporation" encompasses permeabilization of the cell membrane through the application of electrical pulses across the cell. In "reversible electroporation" the permeabilization of the cell membrane ceases or reverses at some point in time after the application of the pulse and the cell membrane permeability reverts to normal. The cell survives "reversible electroporation." It is used as a means for introducing chemicals, DNA, or other materials, such as imaging agents, into cells.

The term "irreversible electroporation" also encompasses the permeabilization of the cell membrane through the application of electrical pulses across the cell. However, in "irreversible electroporation" the permeabilization of the cell membrane does not cease or reverse after the application of the pulse. Thus, the cell membrane permeability does not revert to normal. The cell does not survive "irreversible electroporation" and the cell death is caused by the disruption of the cell membrane and not merely by internal perturbation of cellular components. Openings in the cell membrane are created and/or expanded in size resulting in a fatal disruption in the normal controlled flow of material across the cell membrane. The cell membrane is highly specialized in its ability to regulate what leaves and enters the cell. Irreversible electroporation destroys that ability to regulate in a manner such that the cell can not compensate and as such the cell dies.

By the term "chemotherapeutic agent" is meant any chemotherapeutic agent and it includes but is not limited to,
  i. an aromatase inhibitor,
  ii. an anti-estrogen, an anti-androgen (especially in the case of prostate cancer) or a gonadorelin agonist,
  iii. a topoisomerase I inhibitor or a topoisomerase II inhibitor,
  iv. a microtubule active agent, an alkylating agent, an antineoplastic antimetabolite or a platin compound,
  v. a compound targeting/decreasing a protein or lipid kinase activity or a protein or lipid phosphatase activity, a further anti-angiogenic compound or a compound which induces cell differentiation processes,
  vi. a bradykinin 1 receptor or an angiotensin II antagonist,
  vii. a cyclooxygenase inhibitor, a bisphosphonate, a histone deacetylase inhibitor, a heparanase inhibitor (prevents heparan sulphate degradation), e.g. PI-88, a biological response modifier, preferably a lymphokine or interferons, e.g. interferon, an ubiquitination inhibitor, or an inhibitor which blocks anti-apoptotic pathways,
  viii. an inhibitor of Ras oncogenic isoforms, e.g. H-Ras, K-Ras or N-Ras, or a farnesyl transferase inhibitor, e.g. L-744,832 or DK8G557,
  ix. a telomerase inhibitor, e.g. telomestatin,
  x. a protease inhibitor, a matrix metalloproteinase inhibitor, a methionine aminopeptidase inhibitor, e.g. bengamide or a derivative thereof, or a proteosome inhibitor, e.g. PS-341, and/or
  xi. a mTOR inhibitor.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. A combination of the invention comprising a chemotherapeutic agent which is an aromatase inhibitor is particularly useful for the treatment of hormone receptor positive tumors, e.g. breast tumors.

The term "anti-estrogen" as used herein relates to a compound that antagonizes the effect of estrogens at the estrogen receptor level. The term includes, but is not limited to tamoxifen, fulvestrant, raloxifene and raloxifene hydrochloride. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide.

The term "gonadorelin agonist" as used herein includes, but is not limited to abarelix, goserelin and goserelin acetate.

The term "topoisomerase I inhibitor" as used herein includes, but is not limited to topotecan, irinotecan, 9-nitrocamptothecin and the macromolecular camptothecin conjugate PNU-166148 (compound A1 in WO99/17804).

The term "topoisomerase II inhibitor" as used herein includes, but is not limited to the anthracyclines such as doxorubicin, daunorubicin, epirubicin, idarubicin and nemorubicin, the anthraquinones mitoxantrone and losoxantrone, and the podophillotoxines etoposide and teniposide.

Various anti-tumor antibiotics include the drugs actinomycin-D, bleomycin, and mitomycin-C.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodermolides and epothilones and derivatives thereof, e.g. epothilone B or a derivative thereof.

The term "alkylating agent" as used herein includes, but is not limited to busulfan, chlorambucil, cyclophosphamide, ifosfamide, melphalan or nitrosourea (BCNU or GLIADEL).

The term "antineoplastic antimetabolite" includes, but is not limited to 5-fluorouracil, capecitabine, gemcitabine, cytarabine, fludarabine, thioguanine, methotrexate and edatrexate.

The term "platin compound" as used herein includes, but is not limited to carboplatin, cis-platin and oxaliplatin.

The term "compounds targeting/decreasing a protein or lipid kinase activity or further anti-angiogenic compounds" as used herein includes, but is not limited to protein tyrosine kinase and/or serine and/or threonine kinase inhibitors or lipid kinase inhibitors.

By "antibody" is meant intact monoclonal antibodies, polyclonal antibodies, multispecific antibodies formed from at least 2 intact antibodies, and antibody fragments so long as they exhibit the desired biological activity.

By "capillary" is meant the smallest of a body's blood vessels. Generally, the diameter of a capillary may range from 1 μm to 10 μm, such as from between 3 μm to 8 μm, and including from between, 4 μm to 7 μm, e.g., from between 5 μm to 6 μm. Capillaries connect arterioles and venules, and enable the interchange of water, oxygen, carbon dioxide, and many other nutrient and waste chemical substances between blood and surrounding tissues.

The term "treating" or "treatment" of a condition or disease includes providing a clinical benefit to a subject, and includes: (1) inhibiting the disease, i.e., arresting or reducing the development of the disease or its symptoms, or (2) relieving the disease, i.e., causing regression of the disease or its clinical symptoms.

The term "endothelial cells" means those cells making up the endothelium, the monolayer of simple squamous cells which lines the inner surface of the circulatory system. These cells retain a capacity for cell division, although they proliferate very slowly under normal conditions, undergoing cell division perhaps only once a year. The proliferation of endothelial cells can be demonstrated by using [$^3$H] thymidine to label cells in the S phase. In normal vessels the proportion of endothelial cells that become labeled is especially high at branch points in arteries, where turbulence and wear seem to stimulate turnover. (Goss, R. J., 1978, The Physiology of Growth, Academic Press, New York, pp. 120-137). Normal endothelial cells are quiescent i.e., are not dividing and as such are distinguishable from angiogenic endothelial cells as discussed below.

Endothelial cells also have the capacity to migrate, a process important in angiogenesis. Endothelial cells form new capillaries in vivo when there is a need for them, such as during wound repair or when there is a perceived need for them as in tumor formation. The formation of new vessels is termed angiogenesis, and involves molecules (angiogenic factors) which can be mitogenic or chemoattractant for endothelial cells (Klagsburn, supra). During angiogenesis, endothelial cells can migrate out from an existing capillary to begin the formation of a new vessel i.e., the cells of one vessel migrate in a manner which allows for extension of that vessel (Speidel, C. C., Am J. Anat. 52: 1-79). In vitro studies have documented both the proliferation and migration of endothelial cells; endothelial cells placed in culture can proliferate and spontaneously develop capillary tubes (Folkman, J., and Haudenschild, C., 1980, Nature 288:551-56).

The terms "angiogenic endothelial cells" and "endothelial cells undergoing angiogenesis" and the like are used interchangeably herein to mean endothelial cells undergoing angiogenesis. Thus, angiogenic endothelial cells are endothelial cells which are proliferating at a rate far beyond the normal condition of undergoing cell division roughly once a year. The rate of differentiation from normal proliferation of endothelial cells may be 2×, 5×, or 10× or more that of normal proliferation and can vary greatly depending on factors such as the age and condition of the patient, the type of tumor involved, the type of wound, etc. Provided the difference in the degree of proliferation between normal endothelial cells and angiogenic endothelial cells is measurable and considered biologically significant then the two types of cells are differentiable per the present invention, i.e., angiogenic endothelial cells differentiable from corresponding, normal, quiescent endothelial cells in terms of preferential binding of detectable endothelial cell binding agents.

A "binding agent", as used herein, refers to one member of a binding pair, including an immunologic pair, e.g., a binding moiety that is capable of binding to an antigen, preferably but not limited to a single epitope expressed on the antigen, such as a predetermined tumor antigen. In some embodiments of the invention, the binding agent, when bound to the antigen, forms an immunogenic complex. In one embodiment, the binding agents encompass antibodies.

By "endothelial cell binding agent" is meant one member of a binding pair, wherein said agent many contain, not exclusively, an Fc portion, complement-fixing components or carbohydrates that are capable of binding to a receptor on an endothelial cell.

In one embodiment of the present invention, a binding agent encompasses antigen-binding peptides; receptor-specific proteins; a carbohydrate binding to a receptor; a polypeptide; a glycoprotein; a lipoprotein; and any of the above joined to a molecule that mediates an effector function; as well as mimics or fragments of any of the above. The binding agents of the present invention may be labeled or unlabeled. Binding agents of the present invention can be further engineered to create a fusion protein wherein the first portion of the fusion protein contains a portion that binds to the tumor target cell antigen as described above, and the second portion of the fusion protein contains an Fc portion, complement-fixing components or carbohydrates that are capable of binding to a receptor on an endothelial cell.

The term "selectively associates" and "selectively targets" and the like are used herein to describe a property of binding agents used in the invention which cause a chemotherapeutic agent to associate with angiogenic endothelial cells to a higher degree than the binding agents associate with corresponding normal endothelial cells not involved in angiogenesis. In accordance with the invention selective or preferential association means that the binding agent will associate to a five-fold or higher degree with the endothelial cells undergoing angiogenesis as compared with the corresponding normal endothelial cells not undergoing angiogenesis. More preferably, the preferable or selective association indicates a ten-fold or greater selectivity between angiogenic endothelial cells and corresponding normal endothelial cells.

The term "cancer" refers to a disease of inappropriate (abnormally high) cell proliferation. This derangement is most evident clinically when tumor tissue bulk compromises the function of vital organs. Concepts describing normal tissue growth are applicable to malignant tissue because normal and malignant tissues can share similar growth characteristics, both at the level of the single cell and at the level of the tissue. Cancer is as much a disease of disordered tissue growth regulation as of disordered cellular growth regulation. Doubling time refers to the time required for a tissue or tumor to double in size or cell number. The doubling time of a clinically apparent tumor is usually considerably longer than the cell cycle time of the cells of which the tumor is composed. However, unlike a tumor, the normal liver, heart, or lungs in an adult do not have a doubling time as the organs are in steady state so that the rates of cell production and cell death are equal (Stockdale, F., 1996, "Cancer growth and chemotherapy," in: Scientific American Medicine, vol. 3, Scientific American Press, New York, pp. 12-18). The growth characteristics of tumors are such that new cell production exceeds cell death; a neoplastic event tends to produce an increase in the proportion of stem cells undergoing self-renewal and a corresponding decrease in the proportion progressing to maturation (McCulloch, E. A., et al., 1982, "The contribution of blast cell properties to outcome variation in acute myeloblastic leukemia (AML), Blood 59:601-608). For each tumor population, a doubling time exists and a specific growth curve can be established (Stockdale, F., supra). The growth pattern in tumors can be described by a gomperzian curve (Steel, G. G., 1977, Growth kinetics of tumors, Oxford University Press, Inc., New York, p. 40), which indicates that during the development of a tumor the growth rate is initially very rapid and then progressively decreases as size increases.

INVENTION IN GENERAL

The present invention is a result of the new finding that tumor regression is enhanced by in vivo electroporation, which can be used as a drug delivery system for chemotherapeutics and to retard capillary blood supply to tumors. Specifically, the inventors have found that: a) irreversible electroporation can cause permanent occlusion of capillaries, b) it can cause disintegration, clogging and trapping of cells in the capillaries the area that was irreversible electroporated and c) it can also cause trapping of any kind of compound present at that location at the instant of irreversible electroporation in the region that was electroporated.

The discovery that with irreversible electroporation the occlusion of capillary blood flow in the irreversible electroporated area is permanent has important applications as described below.

Irreversible electroporation may be used to occlude capillary blood flow and blood supply in an undesirable region of tissue so as to induce cell death by ischemia in the region that was irreversible electroporated. This is substantially different from other uses of electrical pulses for tissue ablation which are for the destruction of individual cells and which do not address capillaries. The advantage of using irreversible electroporation to occlude capillary blood flow is that cell death by ischemia is absolute over the entire region in which blood ceases to flow—while cell destruction by electroporation needs to address each cell individually and may suffer from a statistical probability that some cells may survive. Occlusion of capillary blood flow and induction of ischemia by chemical methods has been considered as a method for the treatment of cancer. Irreversible electroporation provides a very efficient method for occluding capillary blood flow without the need for chemicals.

Figure 14:
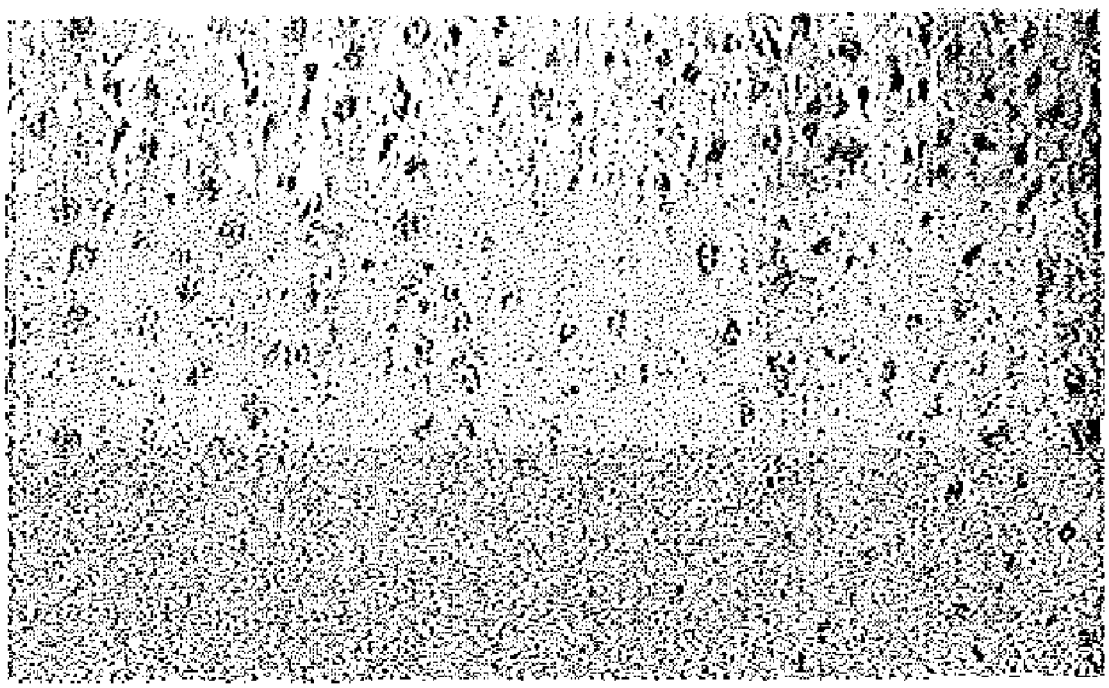
FIG. 14 is an actual photo of a micrograph of the interface between irreversible electroporated liver and normal liver. The left hand side shows normal hepatocytes with clear nucleus and nuclei, well defined cell membrane and clean (flushed) sinusoids. The right hand side shows condensed nuclei, no evidence of cell membrane, expanded cell border with no evidence of sinusoids. Disintegrated red blood cells are in what could have been the spaces of the sinusoids. No effect of flushing.

FIG. 14 shows that red blood cells have become trapped and disintegrated in the irreversible electroporation area. This shows that drugs may be loaded in vesicles or liposomes (a standard method for drug delivery) and the irreversible electroporation can cause the vesicles to disintegrate in the electroporated region. This provides for the delivery of a drug directly to that region.

The results provided here also show that there is no capillary blood flow in the irreversible electroporated region which shows that drugs which are injected systemically in the body blood flow circulation would be entrapped in capillaries via irreversible electroporation. These drugs could be designed to produce any desired effects. Further, the drugs could be in controlled release formulations and be slowly delivered to the tissue surrounding the electroporated area as well as to cells in the electroporated area. Drugs trapped in this manner would not be washed out of the body through the kidneys or metabolized by the liver and therefore would have a long term effect. The drugs could be for destruction of cancer and they could act on possible cancer cells that have survive in the electroporated zone or the area immediately surrounds this area. It should be emphasized that the drugs discussed here are substantially different from those used in reversible electroporation. More specifically, drugs used in reversible electroporation are restricted to those that normally cannot easily penetrate the cell membrane and the reversible electroporation is used to introduce these drugs in the cells.

The typical drugs are bleomycin and Cis-platinum. Using capillary blood flow occlusion with irreversible electroporation allows any kind of drug to be employed because the mechanism for using the drugs is different. Here we do not promote the transport of the drug across the cell membrane but rather the retention of the drug in capillaries in the irreversible electroporated area for long periods of time. This, for instance, would allow the injection in the local blood stream or the interstitial tissue immediately upstream of the area of the tissue to be ablated of extremely high concentrations of a drug. Such high concentrations would be very detrimental to the body if injected systemically. The irreversible electroporation traps the drugs and allows them to be released slowly through the diffusion process, in the area in which they are most needed. The process of diffusion is substantially slower than the convection by blood.

Another method to utilize the blood occlusion for delivery of drugs is to inject after the irreversible electroporation in the electroporated region the drug. The blood occlusion will ensure that the drug is trapped in capillaries in this area.

In addition to drugs other types of chemicals or additives can be trapped inside the irreversible electroporated region. An important application compresses the use of imaging markers—such as gadolinium for MRI or markers for ultrasound or CT. These markers are injected and used to image the area that was irreversible electroporated using any imaging technique relevant to the markers and/or area.

The invention provides a method and a system for capillary blood flow disruption to a targeted area resulting in destruction (ablation) of undesirable tissue in the targeted area. One embodiment of the invention involves the insertion (bringing) electroporation electrodes to the vicinity of the undesirable tissue and in good electrical contact with the tissue and the application of electrical pulses that cause irreversible electroporation of the cells throughout the entire area of the undesirable tissue. In another embodiment a blood vessel or group of blood vessels are targeted at a point or points immediately upstream of a flow of blood to an area of undesired tissue. By disrupting blood flow through the vessel or vessels the cells of the tissue of the targeted area are killed even without directly subjecting cells of the undesired tissue to irreversible electroporation. The cells whose membrane was irreversible permeabilized as well as those whose capillary blood supply has been disrupted may be left in situ (not removed) and as such may be gradually removed by the body's immune system. Cell death is produced by inducing the electrical parameters of irreversible electroporation in the undesirable area.

Electroporation protocols involve the generation of electrical fields in tissue and are affected by the Joule heating of the electrical pulses. When designing tissue electroporation protocols it is important to determine the appropriate electrical parameters that will maximize tissue permeabilization without inducing deleterious thermal effects. It has been shown that substantial volumes of tissue can be electroporated with reversible electroporation without inducing damaging thermal effects to cells and has quantified these volumes (Davalos, R. V., et al., Theoretical analysis of the thermal effects during in vivo tissue electroporation. Bioelectrochemistry, 2003. Vol 61(1-2): p. 99-107). In accordance with the present invention unwanted thermal damage can be further reduced. This can be accomplished by applying current to a smaller area and disrupting capillary blood flow to a larger area and thereby ablating tissue in the larger area which is deprived of capillary blood flow.

The electrical pulses required to induce irreversible electroporation in tissue are larger in magnitude and duration from the electrical pulses required for reversible electroporation. Further, the duration and strength of the pulses required for irreversible electroporation are different from other methodologies using electrical pulses such as for intracellular electro-manipulation or thermal ablation. The methods are very different even when the intracellular (nano-seconds) electro-manipulation is used to cause cell death, e.g. ablate the tissue of a tumor or when the thermal effects produce damage to cells causing cell death.

Typical values for pulse length for irreversible electroporation are in a range of from about 5 microseconds to about 62,000 milliseconds or about 75 microseconds to about 20,000 milliseconds or about 100 microseconds±10 microseconds. This is significantly longer than the pulse length generally used in intracellular (nano-seconds) electro-manipulation which is 1 microsecond or less—see published U.S. application 2002/0010491 published Jan. 24, 2002.

The pulse is at voltage of about 100 V/cm to 7,000 V/cm or 200 V/cm to 2000 V/cm or 300V/cm to 1000 V/cm about 600 V/cm±10% for irreversible electroporation. This is substantially lower than that used for intracellular electro-manipulation which is about 10,000 V/cm, see U.S. application 2002/0010491 published Jan. 24, 2002.

The voltage expressed above is the voltage gradient (voltage per centimeter). The electrodes may be different shapes and sizes and be positioned at different distances from each other. The shape may be circular, oval, square, rectangular or irregular etc. The distance of one electrode to another may be 0.5 to 10 cm., 1 to 5 cm., or 2-3 cm. The electrode may have a surface area of 0.1-5 sq. cm. or 1-2 sq. cm.

The size, shape and distances of the electrodes can vary and such can change the voltage and pulse duration used. Those skilled in the art will adjust the parameters in accordance with this disclosure to obtain the desired degree of electroporation and avoid thermal damage to surrounding cells.

Thermal effects require electrical pulses that are substantially longer from those used in irreversible electroporation (Davalos, R. V., et al., Theoretical analysis of the thermal effects during in vivo tissue electroporation. Bioelectrochemistry, 2003. Vol 61(1-2): p. 99-107). FIG. 1 is showing that irreversible electroporation pulses are longer and have higher amplitude than the reversible electroporation pulses. When using irreversible electroporation for tissue ablation, there may be concern that the irreversible electroporation pulses will be as large as to cause thermal damaging effects to the surrounding tissue and the extent of the tissue ablated by irreversible electroporation will not be significant relative to that ablated by thermal effects. Under such circumstances irreversible electroporation could not be considered as an effective tissue ablation modality as it will act in superposition with thermal ablation. To a degree, this problem is addressed via the present invention. Specifically, capillary blood vessels supplying blood to a tumor can be targeted. When the flow is disrupted the tumor cells die even when the tumor cells themselves may not have been subjected to irreversible electroporation.

The present invention evaluates, through mathematical models and experiment, the maximal extent of tissue ablation that could be accomplished by irreversible electroporation prior to the onset of thermal effects. The models focused on electroporation of liver tissue with two and four needle electrodes and on electroporation of liver tissue with two infinite parallel plates using available experimental data. The experiment (EXAMPLE 3) evaluates irreversible electroporation between two cylindrical electrodes, also in the liver. The liver was chosen because it is considered a potential candidate for irreversible electroporation ablation. The results show that the area that can be ablated by irreversible electroporation prior to the onset of thermal effects is comparable to that which can be ablated by electrochemotherapy, validating the use of irreversible electroporation as a potential minimally invasive surgical modality.

The results obtained by disrupting capillary blood flow to a given area are dramatically shown in FIG. 14 which is a photo of a micrograph. This micrograph is from the interface between irreversible electroporated liver and normal liver. The left hand side shows normal hepatocytes with clear nucleus and nuclei. The photo shows well defined cell membranes and clean (flushed) sinusoids. The right hand side of FIG. 14 shows condensed nuclei, no evidence of cell membrane, expanded cell border with no evidence of sinusoids. The disintegrated red blood cells shown in FIG. 14 are in what could have been the spaces of the sinusoids. Flushing is not believed to have had an effect on the results obtained on the right hand side of FIG. 14.

Earlier studies have shown that the extent of electroporation can be imaged in real time with electrical impedance tomography (EIT) (Davalos, R. V., et al., A feasibility study for electrical impedance tomography as a means to monitor tissue electroporation for molecular medicine. IEEE Transactions on Biomedical Engineering, 2002. 49(4): p. 400-403). In irreversible electroporation the electroporated area persists indefinitely after the electroporation pulse, showing that irreversible electroporation may be imaged leisurely with EIT. Irreversible electroporation, therefore, has the advantage of a tissue ablation technique that is as easy to apply as high temperature ablation, without the need for adjuvant chemicals as electrochemotherapy and with real-time control of the affected area with electrical impedance tomography. Further, in accordance with the invention various types of imaging and monitoring technologies can be used to determine blood flow into and out of a specific area of targeted tissues. These monitoring technologies can be used with the present invention with or without the use of imaging agents which may be added to the blood.

Embolotherapy

The invention can be used with high volume procedures including uterine fibroid embolization (UFE) and targeted liver embolization (TLE).

Uterine fibroids are benign tumors which can cause symptoms such as excessive bleeding, pain and disfigurement. If left untreated, the symptoms can persist until menopause, which severely impacts the patient's quality of life. They afflict approximately 25 million women in the U.S. Industry sources indicate that 200,000-300,000 of the 600,000 hysterectomies performed in the U.S. each year are due to fibroids. Further, there is a large pool of approximately six million women in the U.S. who are symptomatic enough to see their doctor. Today, many of these women take drugs that are not curative and often have severe side effects such as osteoporosis, or they go untreated.

UFE is the occlusion of the blood supply to uterine fibroids to reduce their size and alleviate associated symptoms. Uterine fibroids afflict approximately 25 million women in the U.S., cause mild to moderate symptoms in approximately 6 million, and over 200,000 to undergo surgical procedures.

Uterine Fibroid Embolization

The primary surgical procedures for uterine fibroids are hysterectomy and myomectomy, both of which often are accompanied by complications and long recovery periods.

Driven by demand from women for minimally invasive procedures, the UFE market is projected to grow from 5,000 procedures and under $10 million in 1998 to more than 300,000 procedures and over $500 million by 2004.

TLE is the occlusion of the capillary blood supply to liver tumors to deprive them of the nutrients they require to survive. Over four million people in the U.S. are positive for Hepatitis C which is thought to be a precursor to liver cancer in 10 to 20 percent of these individuals. Thus, the need for the present invention will increase as there is likely to be a significant increase in the incidence of liver cancer in the U.S. in the coming years. The present invention can be used with imaging materials and material such as such as embosphere micro spheres can be used to block the flow of blood to liver tumors.

Embolization is also used in neurointerventions (in the brain and spinal cord) and other parts of the body to occlude the blood flow to hyper vascularized tumors. While not high volume, these are often intricate procedures, especially in the brain, that require an embolic material that can pass through a micro catheter easily and be targeted precisely as can be carried out with the present invention.

The methods of the present invention may be aided by the use of commercially available materials such as EMBOGOLD Micro spheres which bring visibility to the procedure. EMBOGOLD Micro spheres were first marketed in the U.S. in September, 2001 and are precisely calibrated, spherical, hydrophilic, micro-porous beads made of an acrylic co-polymer, which is then cross-linked with gelatin. They are colored to facilitate handling and procedural efficiency. They eliminate aggregation in the catheter, unwanted proximal embolization and unpredictable distal embolization due to particle fragmentation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The mathematical model provided here shows that irreversible tissue ablation can affect substantial volumes of tissue, without inducing damaging thermal effects. To this end, the present invention uses the Laplace equation to calculate the electrical potential distribution in tissue during typical electroporation pulses and a modified Pennes (bioheat), (Pennes, H. H., *Analysis of tissue and arterial blood flow temperatures in the resting forearm*. J of Appl. Physiology., 1948. 1: p. 93-122), equation to calculate the resulting temperature distribution. It is important to note that there are several forms of the bioheat equation which have been reviewed (Carney, C. K., *Mathematical models of bioheat transfer*, in *Bioengineering heat transfer*, Y. I. Choi, Editor. 1992, Academic Press, Inc: Boston. p. 19-152; Eto, T. K. and B. Rubinsky, *Bioheat transfer*, in *Introduction to bioengineering*, S. A. Berger, W. Goldsmith, and E. R. Lewis, Editors. 1996, Oxford Press). While the Pennes equation is controversial, it is nevertheless commonly used because it can provide an estimate of the various biological heat transfer parameters, such as blood flow and metabolism. The modified Pennes equation in this study contains the Joule heating term in tissue as an additional heat source.

The electrical potential associated with an electroporation pulse is determined by solving the Laplace equation for the potential distribution:

$$\nabla \cdot (\sigma \nabla \phi) = 0 \quad (1)$$

where $\phi$ is the electrical potential and $\sigma$ is the electrical conductivity. The electrical boundary condition of the tissue that is in contact with the leftmost electrode(s) on which the electroporation pulse is applied is:

$$\phi = V_0 \quad (2)$$

The electrical boundary condition at the interface of the rightmost electrode(s) is:

$$\phi = 0 \quad (3)$$

The boundaries where the analyzed domain is not in contact with an electrode are treated as electrically insulative to provide an upper limit to the electrical field near the electroporation electrodes and an upper limit to the temperature distribution that results from electroporation:

$$\frac{\partial \phi}{\partial n} = 0 \quad (4)$$

Solving the Laplace equation enables one to calculate the associated Joule heating, the heat generation rate per unit volume from an electrical field (p):

$$p = \sigma |\nabla \phi|^2 \quad (5)$$

This term is added to the original Pennes equation, (Pennes, H. H., *Analysis of tissue and arterial blood flow temperatures in the resting forearm*. J of Appl. Physiology., 1948. 1: p. 93-122) to represent the heat generated from the electroporation procedure:

$$\nabla \cdot (k \nabla T) + w_b c_b (T_a - T) + q''' + p = \rho c_p \frac{\partial T}{\partial t} \quad (6)$$

To solve equation (4) it is assumed that the entire tissue is initially at the physiological temperature of 37° C.:

$$T(x,y,z,0) = 37 \quad (7)$$

The outer surface of the analyzed domain and the surfaces of the electrodes are taken to be adiabatic, which should produce an upper limit to the calculated temperature distribution in the tissue:

$$\frac{\partial T}{\partial n} = 0 \text{ on the electrodes boundary and the outer surface domain} \quad (8)$$

The analysis modeled conditions typical to tissue electroporation in the liver. The liver was chosen because it is the organ that most minimally invasive ablation techniques treat since cancer in the liver can be resolved by extirpation of the diseased area while surgical resection is not possible in many cases for this organ (Onik, G., B. Rubinsky, and et al., *Ultrasound-Guided Hepatic Cryosurgery in the Treatment of Metastatic Colon Carcinoma*. Cancer, 1991. 67(4): p. 901-907). The electroporation parameters, i.e. pulse parameters for reversible and irreversible electroporation where obtained from rat liver data (Miklavcic, D., et al., *A validated model of in vivo electric field distribution in tissues for electrochemotherapy and for DNA electrotransfer for gene therapy*. Biochimica et Biophysica Acta, 2000. 1523(1): p. 73-83; Suzuki, T., et al., *Direct gene transfer into rat liver cells by in vivo electroporation*. FEBS Letters, 1998. 425(3): p. 436-440), but biological parameters corresponding to the human liver were used in the analysis. Tissue thermal properties are taken from reference (Duck, F. A., *Physical Properties of Tissues: A Comprehensive Reference Book*. 1990, San Diego: Academic Press) and the electrical properties from reference (Boone, K., D. Barber, and B. Brown, *Review—Imaging with electricity: report of the European Concerted Action on Impedance Tomography*. J. Med. Eng. Technol., 1997. 21: p. 201-232) and are listed in table 1. The tissue is assumed isotropic and macroscopically homogeneous. The intent of the analysis was to determine the extent of the region in which reversible or irreversible electroporation is induced in the liver for various electroporation voltages and durations while the maximal temperature in the tissue is below 50° C. Thermal damage is a time-dependent process described by an Arhenius type equation (Henriques, F. C. and A. R. Moritz, *Studies in thermal injuries: the predictability and the significance of thermally induced rate processes leading to irreversible epidermal damage*. Arch Pathol., 1947. 43: p. 489-502; Diller, K. R., *Modeling of bioheat transfer processes at high and low temperatures*, in *Bioengineering heat transfer*, Y. I. Choi, Editor. 1992, Academic Press, Inc: Boston. p. 157-357), $$\Omega = \int \xi e^{-E_a/RT} dt \qquad (9)$$

Where $\Omega$ is a measure of thermal damage, $\xi$ is the frequency factor, $E_a$ is the activation energy and R is the universal gas constant. A detailed description on the various degrees of thermal damage as described in Equation (9) above can be found in (Diller, K. R., *Modeling of bioheat transfer processes at high and low temperatures*, in *Bioengineering heat transfer*, Y. I. Choi, Editor. 1992, Academic Press, Inc: Boston. p. 157-357).

A careful examination shows that the thermal damage is a complex function of time, temperature and all the parameters in Equation (9) above and that there are various degrees of thermal damage. In various applications or for various considerations it is possible to design irreversible electroporation protocols that induce some degree of thermal damage, either in part of the electroporated region or at a reduced level throughout the electroporated region. However, in this example we have chosen 50° C. as the target temperature for several reasons. Thermal damage begins at temperatures higher than 42° C., but only for prolonged exposures. Damage is relatively low until 50° C. to 60° C. at which the rate of damage dramatically increases (Diller, K. R., *Modeling of bioheat transfer processes at high and low temperatures*, in *Bioengineering heat transfer*, Y. I. Choi, Editor. 1992, Academic Press, Inc: Boston. p. 157-357). Therefore 50° C. will be a relatively low bound on the possible thermal effects during irreversible electroporation. It is anticipated that the electrical parameters chosen for irreversible electroporation without a thermal effect could be substantially longer and higher than those obtained from an evaluation for 50° C. in this example. Furthermore, since the Laplace and bioheat equations are linear, the results provided here can be extrapolated and considered indicative of the overall thermal behavior.

The analyzed configurations have two needles or four needle electrodes embedded in a square model of the liver. Needle electrodes are commonly used in tissue electroporation and will be most likely also used in the liver (Somiari, S., et al., *Theory and in vivo application of electroporative gene delivery*. Molecular Therapy, 2000. 2(3): p. 178-187). The square model of the liver was chosen large enough to avoid outer surface boundary effects and to produce an upper limit for the temperature, which develops during electroporation in the liver. For each configuration the surface of one electrode is assumed to have a prescribed voltage with the other electrode set to ground. The effect of the spacing between the electrodes was investigated by comparing distances of 5, 7.5 and 10 mm, which are typical. The electrodes were also modeled with typical dimensions of 0.5, 1 and 1.5 mm in diameter. The blood flow perfusion rate was taken to zero or 1.0 kg/m³ s (Deng, Z. S. and J. Liu, *Blood perfusion-based model for characterizing the temperature fluctuations in living tissue*. Phys A STAT Mech Appl, 2001. 300: p. 521-530). The metabolic heat was taken to be either zero or 33.8 kW/m³ (Deng, Z. S. and J. Liu, *Blood perfusion-based model for characterizing the temperature fluctuations in living tissue*. Phys A STAT Mech Appl, 2001. 300: p. 521-530).

The calculations were made for an electroporation pulse of 800 µs. This pulse duration was chosen because typically, reversible electroporation is done with eight separate 100 µs pulses, (Miklavcic, D., et al., *A validated model of in vivo electric field distribution in tissues for electrochemotherapy and for DNA electrotransfer for gene therapy*. Biochimica et Biophysica Acta, 2000. 1523(1): p. 73-83) and therefore the value we chose is an upper limit of the thermal effect in a pulse time frame comparable to that of reversible electroporation. Consequently, the results obtained here are the lower limit in possible lesion size during irreversible electroporation. It should be emphasized that we believe irreversible electroporation tissue ablation can be done with shorter pulses than 800 µs. To evaluate the thermal effect, we gradually increased in our mathematical model the applied pulse amplitude for the 800 µs pulse length until our calculations indicated that the electroporation probe temperature reached 50° C., which we considered to be the thermal damage limit. Then, we evaluated the electric field distribution throughout the liver.

A transmembrane potential on the order of 1V is required to induce irreversible electroporation. This value is dependent on a variety of conditions such as tissue type, cell size and other external conditions and pulse parameters. The primary electrical parameter affecting the transmembrane potential for a specific tissue type is the amplitude of the electric field to which the tissue is exposed. The electric field thresholds used in estimating the extent of the region that was irreversibly electroporated were taken from the fundamental studies of Miklavcic, Mir and their colleagues performed with rabbit liver tissue (Miklavcic, D., et al., *A validated model of in vivo electric field distribution in tissues for electrochemotherapy and for DNA electrotransfer for gene therapy*. Biochimica et Biophysica Acta, 2000. 1523(1): p. 73-83). In this study, that correlated electroporation experiments with mathematical modeling, they have found that the electric field for reversible electroporation is 362+/−21 V/cm and is 637+/−43 V/cm for irreversible electroporation for rat liver tissue. Therefore, in the analysis an electric field of 360 V/cm is taken to represent the delineation between no electroporation and reversible electroporation and 680 V/cm to represent the delineation between reversible and irreversible electroporation.

All calculations were performed using MATLAB's finite element solver, Femlab v2.2 (The MathWorks, Inc. Natick, Mass.). To ensure mesh quality and validity of solution, the mesh was refined until there was less than a 0.5% difference in solution between refinements. The baseline mesh with two 1 mm electrodes, 10 mm spacing had 4035 nodes and 7856 triangles. The simulations were conducted on a Dell Optiplex GX240 with 512 MB of RAM operating on Microsoft Windows 2000.

Results and Discussion

Figure 2A:
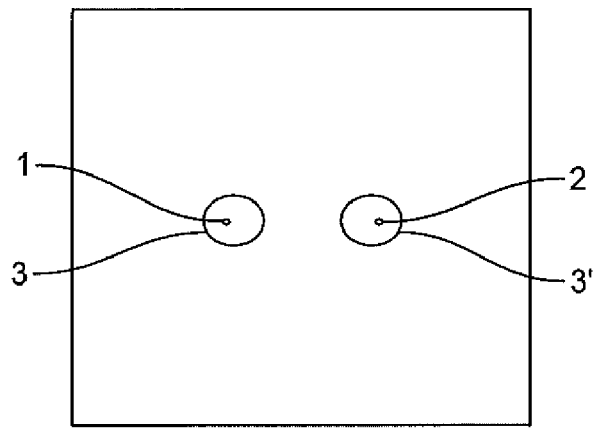
FIGS. 2A, 2B and 2C are each schematic images of irreversibly electroporated areas for two-electrode configurations using 10 mm center-to-center spacing as following for FIGS. 2A, B and C: (2A) 0.5 mm (857V); (2B) 1.0 mm (1295V); (2C) 1.5 mm (1575V) diameter electrodes with a 680V/cm threshold for irreversible electroporation.
Figure 2B:
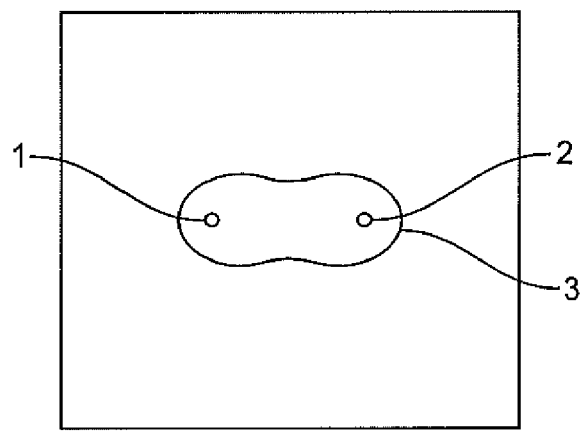
Figure 2C:
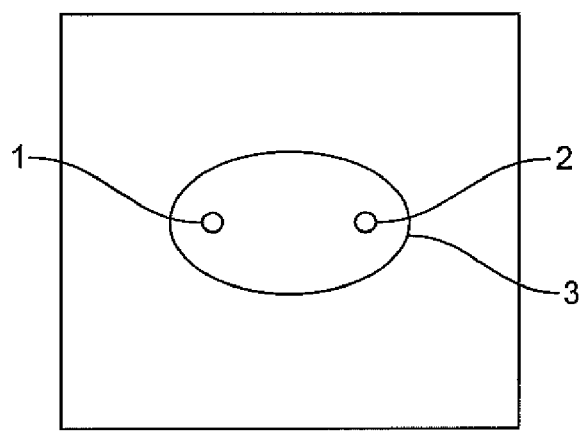
Figure 3A:
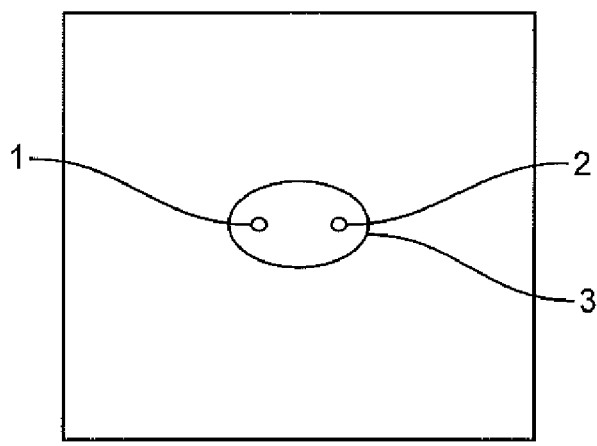
FIGS. 3A, 3B, and 3C are schematic images showing irreversibly electroporated regions using a 680 V/cm threshold for a two-electrode confirmation with 1 mm diameter and 876V and 5 mm spacing for FIGS. 3A; 1116V and 7.5 mm for FIG. 3B; and 1295V and 10 mm spacing for FIG. 3C.
Figure 3B:
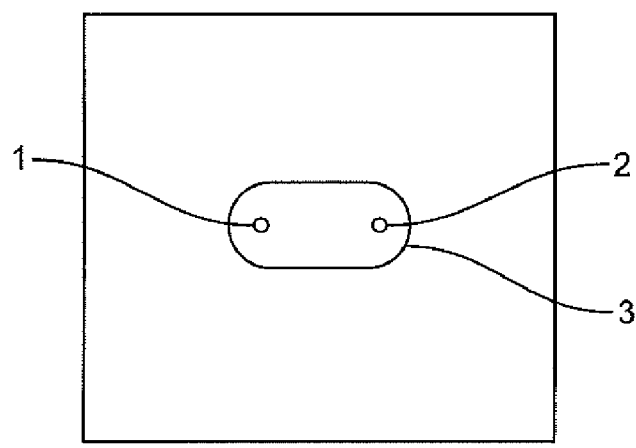
Figure 3C:
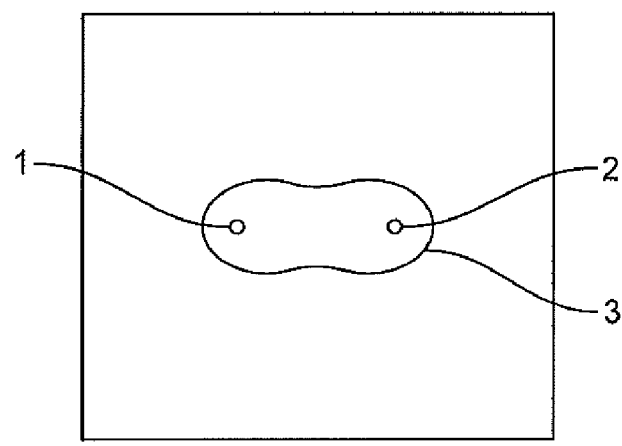

FIGS. 2 and 3 examine the effect of the electrode size and spacing on the ablated area in a two-needle electroporation configuration. In obtaining these figures, we ignored the effect of the blood flow and metabolism in the heat transfer equation, which should give an upper limit for the estimated ablation area. FIG. 2 compares the extent of the irreversible electroporated area for electroporation electrode sizes of 0.5, 1 and 1.5 mm in diameter and a distance between electrodes of 10 mm (FIGS. 2A, 2B and 2C). The strong effect of the electrode size is evident. FIG. 2A shows electrodes 1 and 2. Surrounding electrode 1 is the irreversibly electroporated area 3. Surrounding electrode 2 is the irreversibly electroporated area 4. In FIG. 2B electrodes 1 and 2 are shown with a continuous irreversibly electroporated area 3. It is seen that for the smaller electrodes (FIG. 2A), the irreversibly electroporated area is not contiguous, while for a 1.5 mm electrode the area of potential tissue, ablation has an elliptical shape with dimensions of about 15 mm by 10 mm (FIG. 2C). In the brackets, we give the electroporation voltage for which the probe temperature reaches 50° C. in these three configurations. It is seen that the range is from 857V for the 0.5 mm probe to 1575V for the 1.5 mm probe. This is within the typical range of tissue electroporation pulses. FIG. 3 evaluates the effect of the spacing between the electrodes (FIGS. 3A, 3B and 3C). It is observed that in the tested range, the small dimension of the contiguous elliptical shape of the ablated lesion remains the same, while the larger dimension seems to scale with the distance between the electrodes.

Figure 4A:
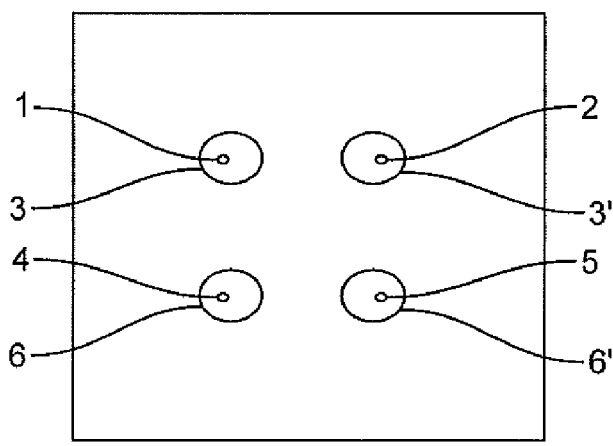
Figure 4B:
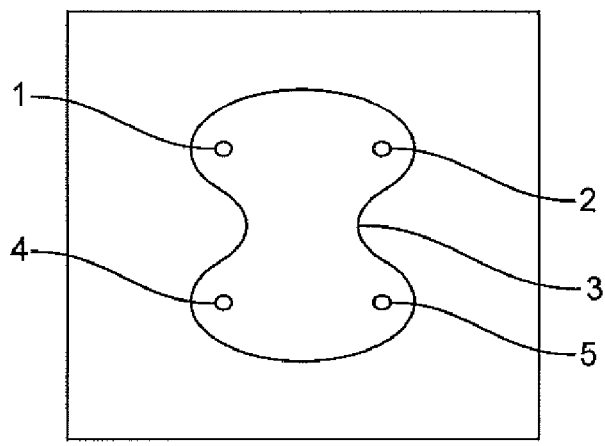
Figure 4C:
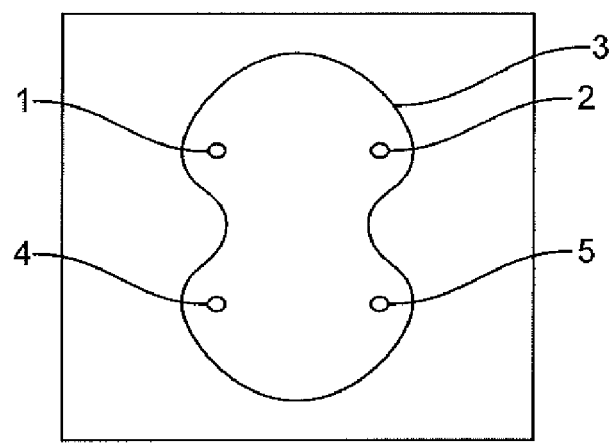
Figure 5A:
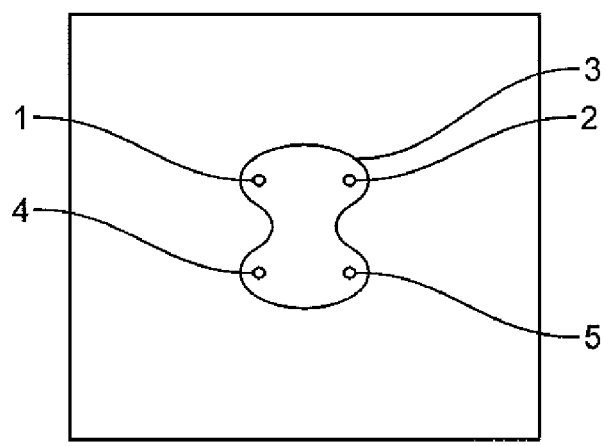
FIGS. 5A, 5B and 5C are schematic images showing the effect of electrode spacing for a 4-electrode configuration wherein the electrode is 1 mm in diameter
Figure 5B:
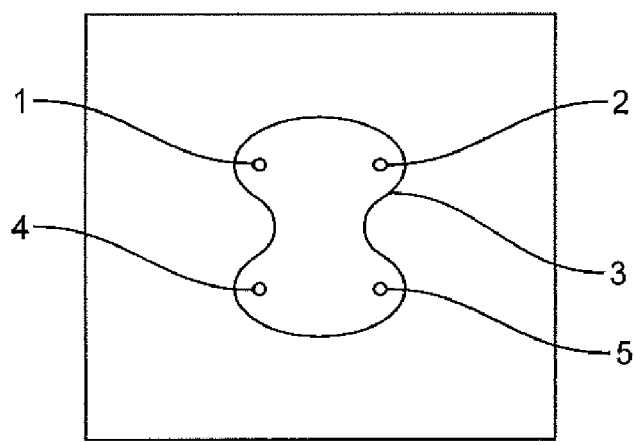
Figure 5C:
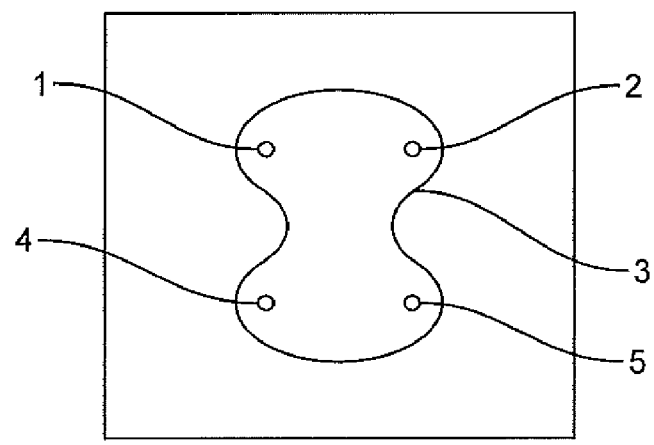

FIGS. 2A, 2B, 2C and 3A, 3B and 3C demonstrate that the extent of tissue ablation with irreversible electroporation is comparable to that of other typical minimally invasive methods for tissue ablation, such as cryosurgery (Onik, G. M., B. Rubinsky, and et. al., *Ultrasound-guided hepatic cryosurgery in the treatment of metastatic colon carcinoma*. Cancer, 1991. 67(4): p. 901-907; Onik, G. M., et al., *Transrectal ultrasound-guided percutaneous radical cryosurgical ablation of the prostate*. Cancer, 1993. 72(4): p. 1291-99). It also shows that varying electrode size and spacing can control lesion size and shape. The shape and size of the ablated lesion can be also controlled by varying the number of electrodes used. This is shown in FIGS. 4 and 5, for a four-electrode configuration. In each of FIGS. 4A, 4B and 4C there are four electrodes shown by 1, 2, 5, and 6. The electrodes 1 and 2 are surrounded, respectively, by irreversibly electroporated areas 3 and 4. The electrodes 5 and 6 are surrounded by irreversibly electroporated areas 7 and 8 in FIG. 4A. In FIGS. 4B and 4C the electrodes 1, 2, 5 and 6 are surrounded by irreversibly electroporated areas 3. The same is shown in FIGS. 5A, 5B and 5C. These figures also compare the effect of probe size and spacing and the results were also obtained by ignoring the effect of blood flow and metabolism in the energy equation.

Again, it is seen that larger electrodes have a substantial effect on the extent of the ablated region and that the extent of ablation scales with the spacing between the electrodes.

Figure 6:
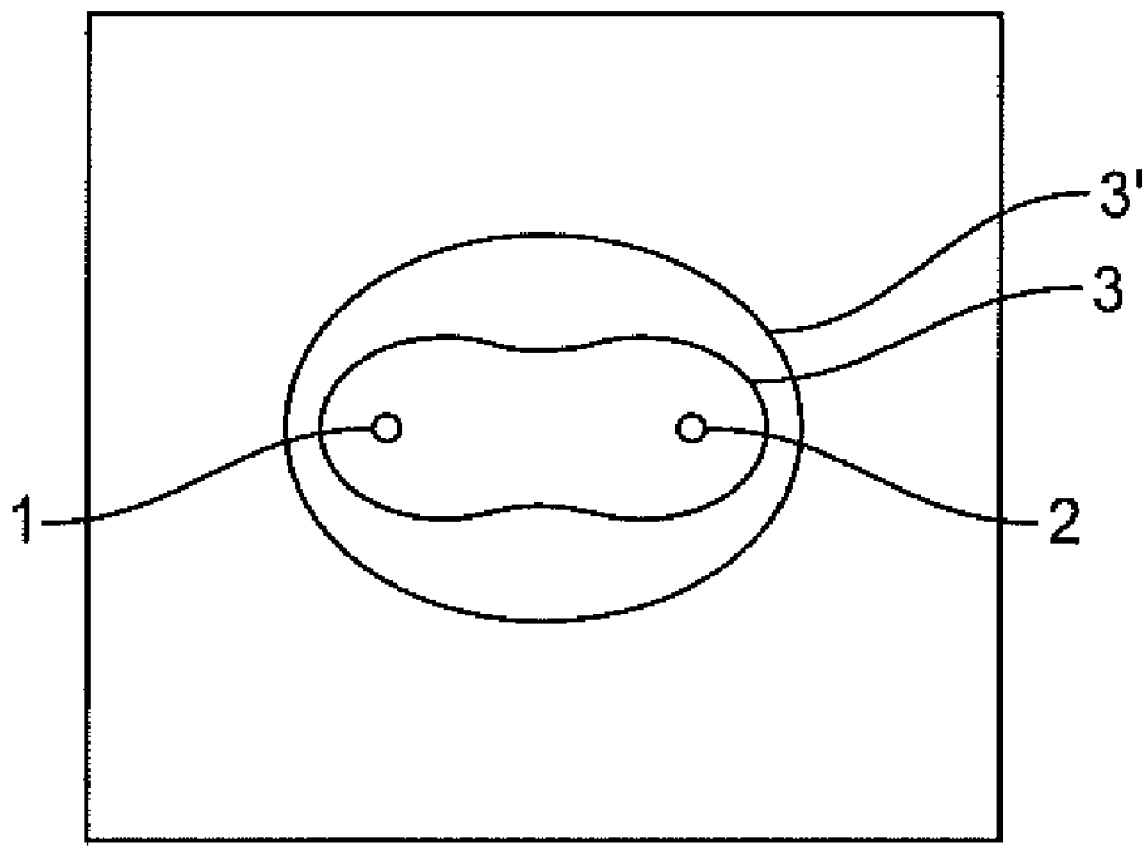
FIG. 6 is a schematic image showing the irreversible (1295V, 680V/cm threshold) as compared to the reversible region (1300V, 360V/cm threshold) using virtually the same electrical parameters. 1300V is the most common voltage applied across two electrodes for ECT. The most common voltage parameters are eight 100 μs pulses at a frequency of 1 Hz. Applying a single 800 μs pulse provides a conservative estimate of the heating associated with a procedure. The one second space normally between pulses will enlarge an area amount of heat to be dissipated through the tissue.
Figure 7:
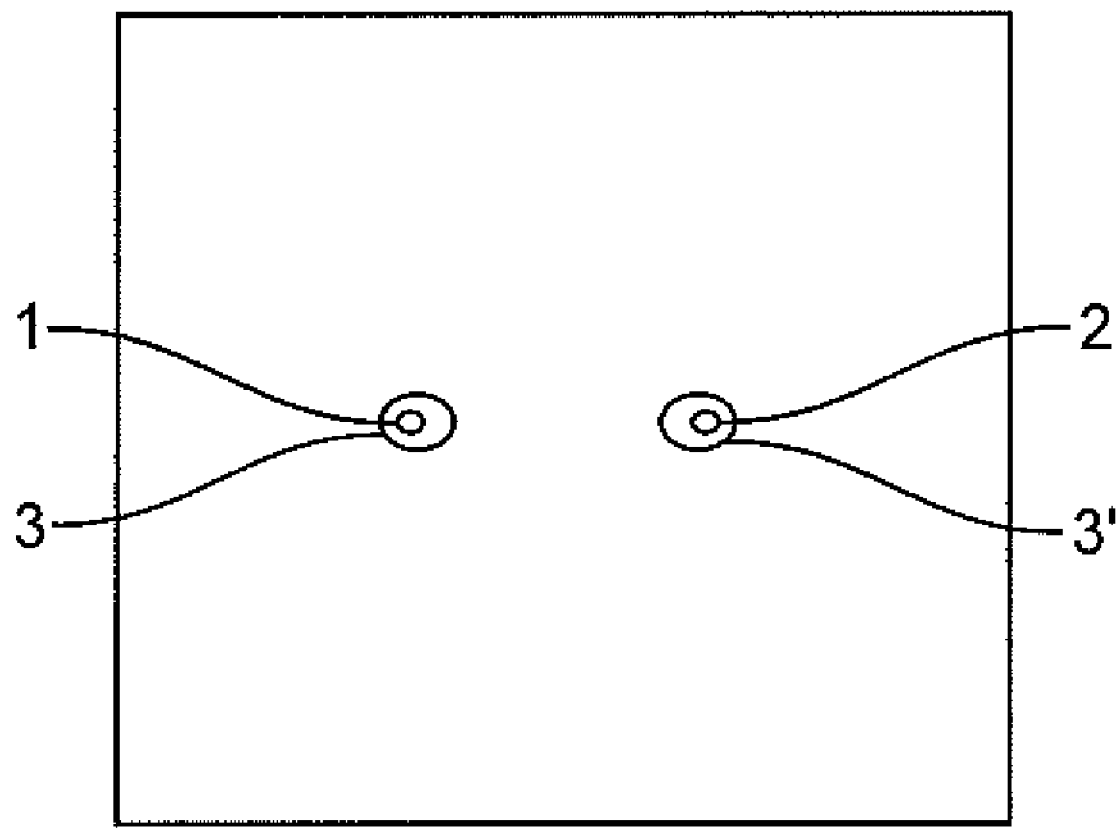

A comparison between reversible and irreversible electroporation protocols can be achieved from FIGS. 6 and 7. In FIG. 6, an 800 μs, 1295 V pulse was applied between two 1.5 mm diameter electrodes placed 10 mm apart. In FIG. 6 electrodes 1 and 2 are surrounded by irreversibly electroporated area 3 and an area 7 where the cells are reversibly electroporated. This produces a tissue temperature lower than 50° C. The figure plots the margin of the irreversibly electroporated region, i.e. the 680 V/cm voltage-to-distance gradients and that of the reversible electroporated region, the 360 V/cm gradients. FIG. 7 was obtained for two 1 mm electrodes placed 10 mm apart. In this figure, we produced an electroporated region that was only reversibly electroporated, i.e. with electric fields lower than 360 V/cm. FIG. 7 shows electrodes 1 and 2 surrounded by cell areas 8 and 9 where the cells are reversibly electroporated. In comparing FIGS. 6 and 7, it is obvious that the extent of the ablated area possible through electrochemotherapy alone is substantially smaller than that through irreversible electroporation alone.

Figure 8A:
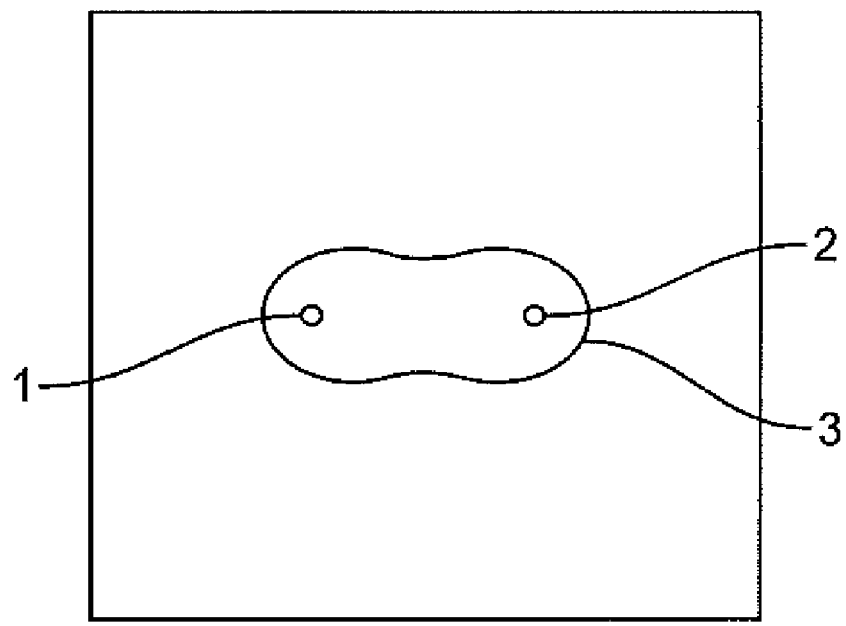
FIGS. 8A and 8B show a schematic comparison of the effect of blood flow and metabolism on the amount of irreversible electroporation.
Figure 8B:
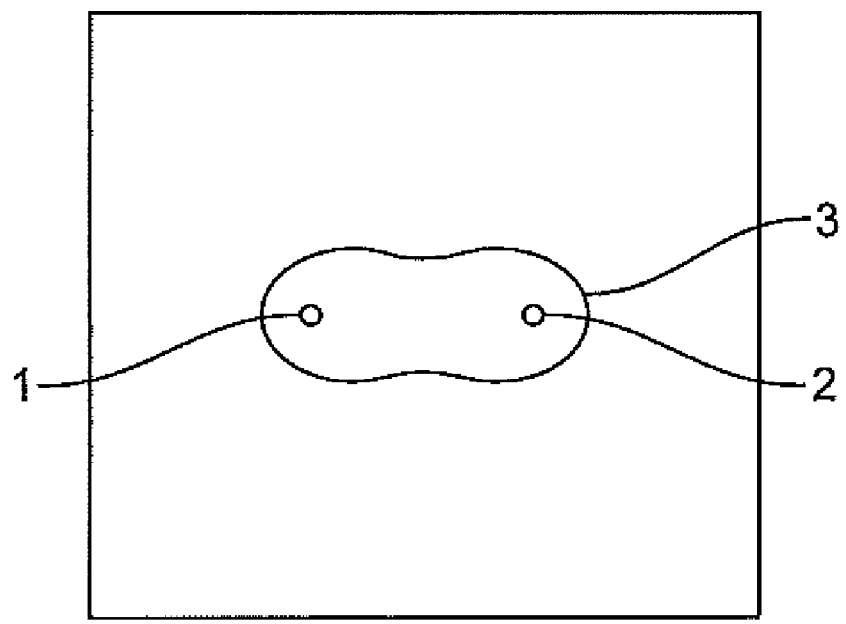

The effect of blood flow and metabolism on the extent of irreversible electroporation is illustrated in FIG. 8. Specifically, FIGS. 8A and 8B each show electrodes 1 and 2 wherein the electrodes are surrounded by cell areas where the cells are irreversibly electroporated. The figures compare a situation with metabolism and a relatively high blood flow rate to a situation without blood flow or metabolism. It is obvious that metabolism and blood perfusion have a negligible effect on the possible extent of irreversible tissue electroporation. This is because the effect of the Joule heating produced by the electroporation current is substantially larger than the effects of blood flow or metabolism.

An even more conservative estimate for the thermal damage can be obtained by assuming that the tissue reaches 50° C. instantaneously, during the electroporation pulses such that the damage is defined as $$\Omega = t_p \xi e^{-E/RT} \tag{10}$$

Several values taken from the literature for activation energy and frequency factor were applied to equation (10) with the pulse lengths calculated in the examples above. Because the application of the pulse is so short, the damage would be near zero, many times less than the value ($\Omega$=0.53) to induce a first degree burn (Diller, K. R., *Modeling of bioheat transfer processes at high and low temperatures*, in *Bioengineering heat transfer*, Y. I. Choi, Editor. 1992, Academic Press, Inc: Boston. p. 157-357). regardless of the values used for activation energy and frequency factor.

Currently, tissue ablation by electroporation is produced through the use of cytotoxic drugs injected in tissue combined with reversible electroporation, a procedure known as electrochemotherapy. The present invention shows that irreversible electroporation by itself produces substantial tissue ablation for the destruction of undesirable tissues in the body. The concern was that higher voltages required for irreversible electroporation would cause Joule heating and would induce thermal tissue damage to a degree that would make irreversible electroporation a marginal effect in tissue ablation. Using a mathematical model for calculating the electrical potential and temperature field in tissue during electroporation, the present invention shows that the area ablated by irreversible tissue electroporation prior to the onset of thermal effects is substantial and comparable to that of other tissue ablation techniques such as cryosurgery. Our earlier studies have shown that the extent of electroporation can be imaged in real time with electrical impedance tomography (Davalos, R. V., et al., *A feasibility study for electrical impedance tomography as a means to monitor tissue electroporation for molecular medicine*. IEEE Transactions on Biomedical Engineering, 2002. 49(4): p. 400-403; Davalos, R. V., et al., *Electrical impedance tomography for imaging tissue electroporation*. IEEE Transactions on Biomedical Engineering, 2004). Irreversible electroporation, therefore, has the advantage of being a tissue ablation technique, which is as easy to apply as high temperature ablation, without the need for adjuvant chemicals as required in electrochemical ablation and electrochemotherapy. In addition, a unique aspect of irreversible electroporation is that the affected area can be controlled in real time with electrical impedance tomography.

Example 2

This example was developed to produce a correlation between electroporation pulses and thermal effects. The system analyzed is an infinitesimally small control volume of tissue exposed to an electroporation voltage gradient of V (Volts/cm). The entire electrical energy is dissipated as heat and there is no conduction of heat from the system. The calculations produce the increase in temperature with time during the application of the pulse and the results are a safe lower limit for how long a certain electroporation pulse can be administered until a certain temperature is reached. To generate the correlation an energy balance is made on a control volume between the Joule heating produced from the dissipation of heat of the V (volt/cm) electrical potential dissipating through tissue with an electrical conductivity of σ (ohm-cm) and the raise in temperature of the control volume made of tissue with a density ρ (g/cc) and specific heat, c, (J/g K). The calculation produces the following equation for the raise in temperature (T) per unit time (t) as a function of the voltage gradients and the thermal and electrical properties of the liver.

$$\frac{dT}{dt} = \frac{V^2 \sigma}{\rho c} \tag{2-1}$$

The table below was obtained for the liver with the following properties:
Electrical resistivity of liver—8.33 Ohm-meter
Specific heat of liver—J/g K
Density of liver—1 g/cc
We obtain the following table:

TABLE 1

| Voltage Gradient - V (V/cm) | Time per degree C. rise (ms) | time from 37 C. to 65 C. (ms) |
|---|---|---|
| 50 | 1199.52 | 33586.56 |
| 100 | 299.88 | 8396.64 |
| 150 | 133.28 | 3731.84 |
| 200 | 74.97 | 2099.16 |
| 250 | 47.98 | 1343.46 |
| 300 | 33.32 | 932.96 |
| 350 | 24.48 | 685.44 |
| 400 | 18.74 | 524.79 |
| 450 | 14.81 | 414.65 |
| 500 | 12.00 | 335.87 |
| 550 | 9.91 | 277.57 |
| 600 | 8.33 | 233.24 |
| 650 | 7.10 | 198.74 |
| 700 | 6.12 | 171.36 |
| 750 | 5.33 | 149.27 |
| 800 | 4.69 | 131.20 |

TABLE 1-continued

| Voltage Gradient - V (V/cm) | Time per degree C. rise (ms) | time from 37 C. to 65 C. (ms) |
|---|---|---|
| 850 | 4.15 | 116.22 |
| 900 | 3.70 | 103.66 |
| 950 | 3.32 | 93.04 |
| 1000 | 3.00 | 83.97 |
| 1050 | 2.72 | 76.16 |
| 1100 | 2.48 | 69.39 |
| 1150 | 2.27 | 63.49 |
| 1200 | 2.08 | 58.31 |
| 1250 | 1.92 | 53.74 |
| 1300 | 1.77 | 49.68 |
| 1350 | 1.65 | 46.07 |
| 1400 | 1.53 | 42.84 |
| 1450 | 1.43 | 39.94 |
| 1500 | 1.33 | 37.32 |

The second column of Table 1 gives the amount of time it takes for the temperature of the liver to raise 1° C., when the tissue experiences the electroporation pulse in column 1. The time for even a relatively high electroporation voltage of 1500V/cm is of the order of 1.33 milliseconds for 1° C. rise and 37.32 milliseconds until a temperature of 65° C. is reached. Using the equation (2-1) or Table 1 it is possible to evaluate the amount of time a certain pulse can be applied without inducing thermal effects. Considering the typical electroporation parameters reported so far there is no limitation in the electroporation length from thermal considerations. Column 3 of Table 1 shows the time required to reach 65° C., which is where thermal damage may begin. The calculations in this example give a lower limit for the extent of time in which a certain thermal effects will be induced by electroporation pulses. For more precise calculations it is possible to use the equation developed in this example with equation (9) or (10) from Example 1.

Example 3

Figure 9:
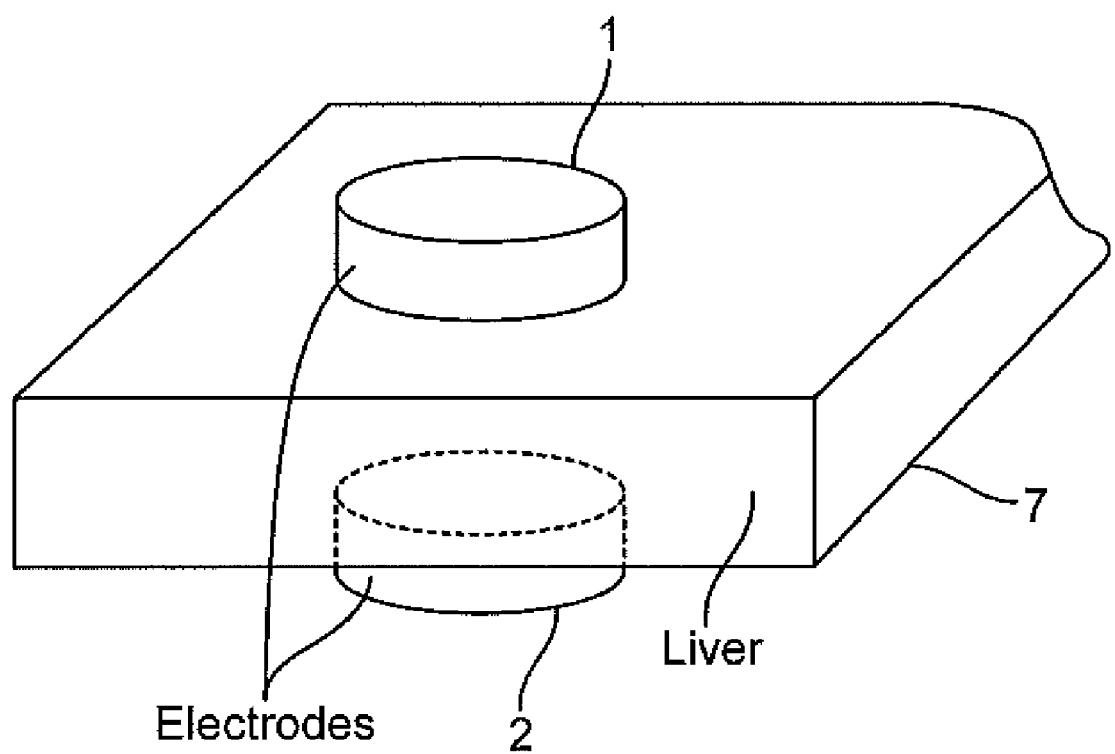
FIG. 9 is a schematic view of liver tissue between two cylindrical Ag/AgCl electrodes. The distance between the electrodes was 4 mm and the radius of the electrodes is 10 mm. The electrodes were clamped with special rig parallel and concentric to each other. The liver lobe was compressed between the electrodes to achieve good contact.
Figure 10:
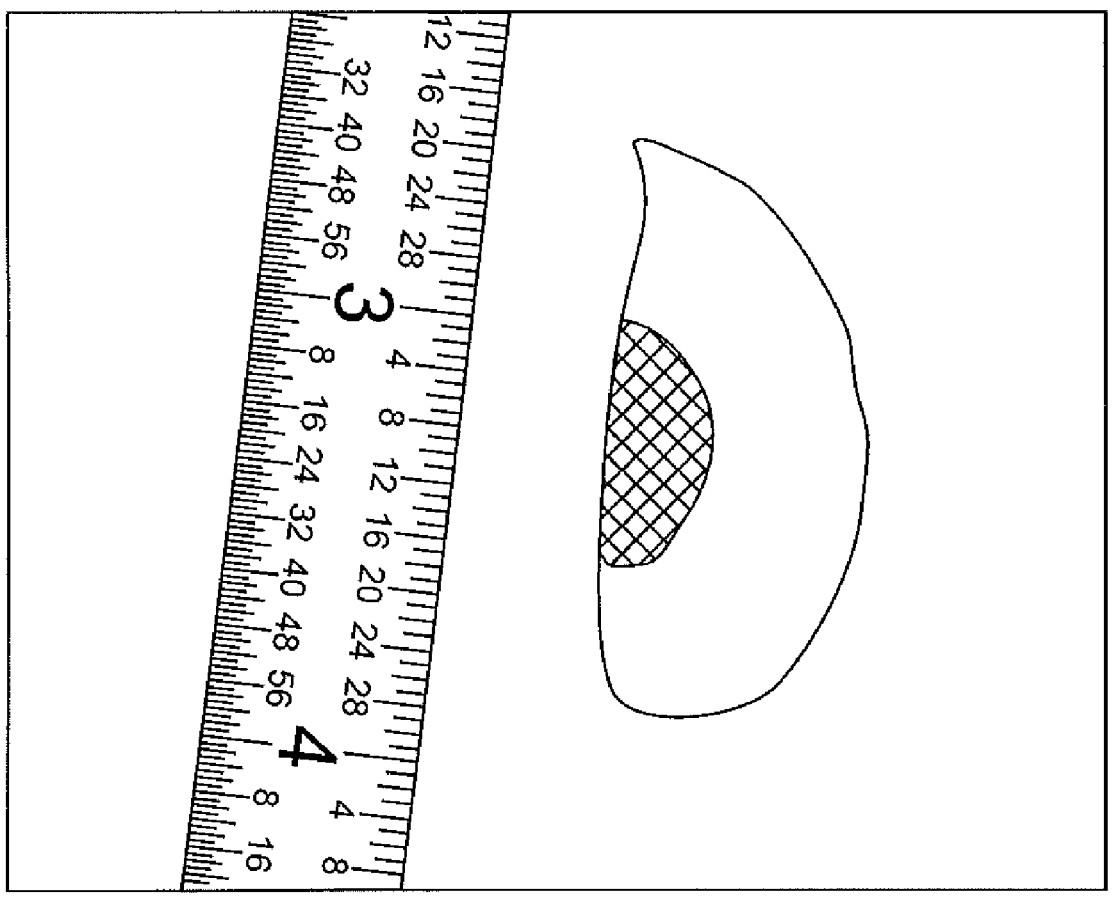
FIG. 10 is an actual photo of a view of a liver which was electroporated by irreversible electroporation with two cylindrical surface electrodes of 10 mm in diameter. Histology shows that the dark area is necrotic.
Figure 11:
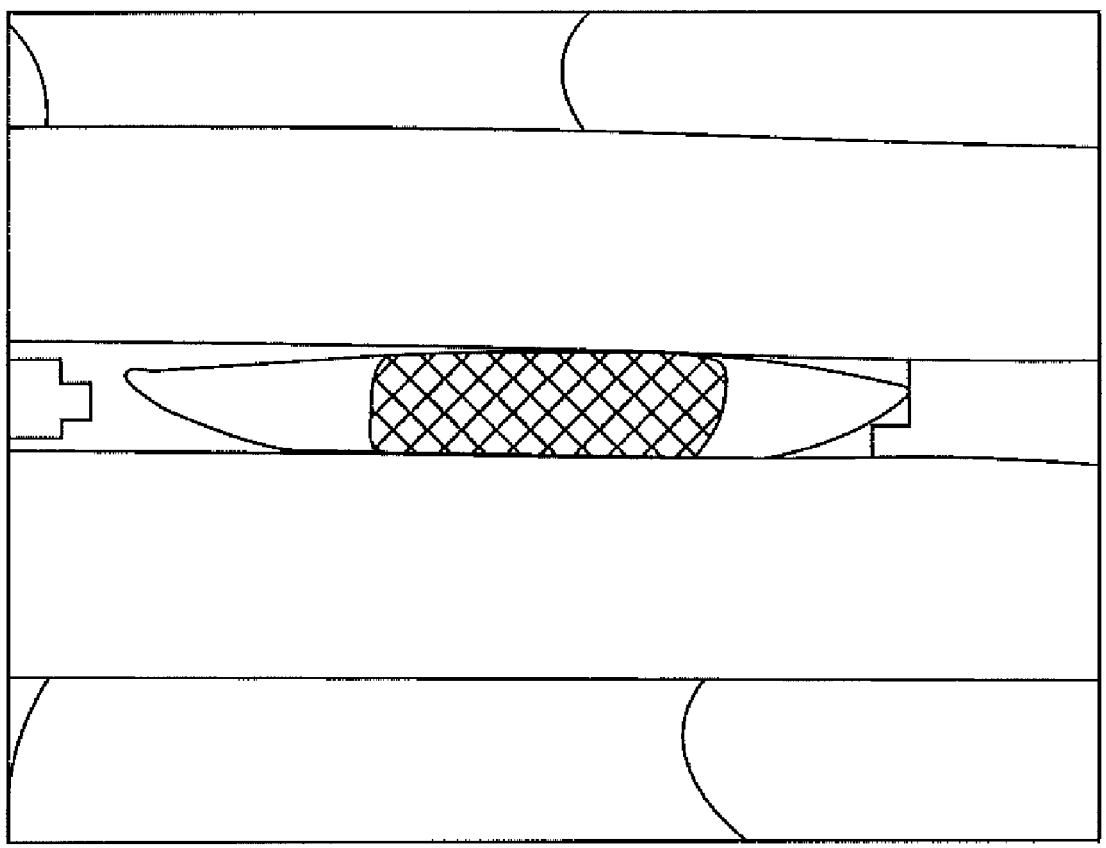
FIG. 11 is an actual photo of a cross section through an electroporated liver. Histology shows that the dark area is necrotic. The distance between the two Al plates that hold the liver is exactly 4 mm. The electroporation electrodes were 10 mm in diameter and centered in the middle of the lesion.
Figure 12:
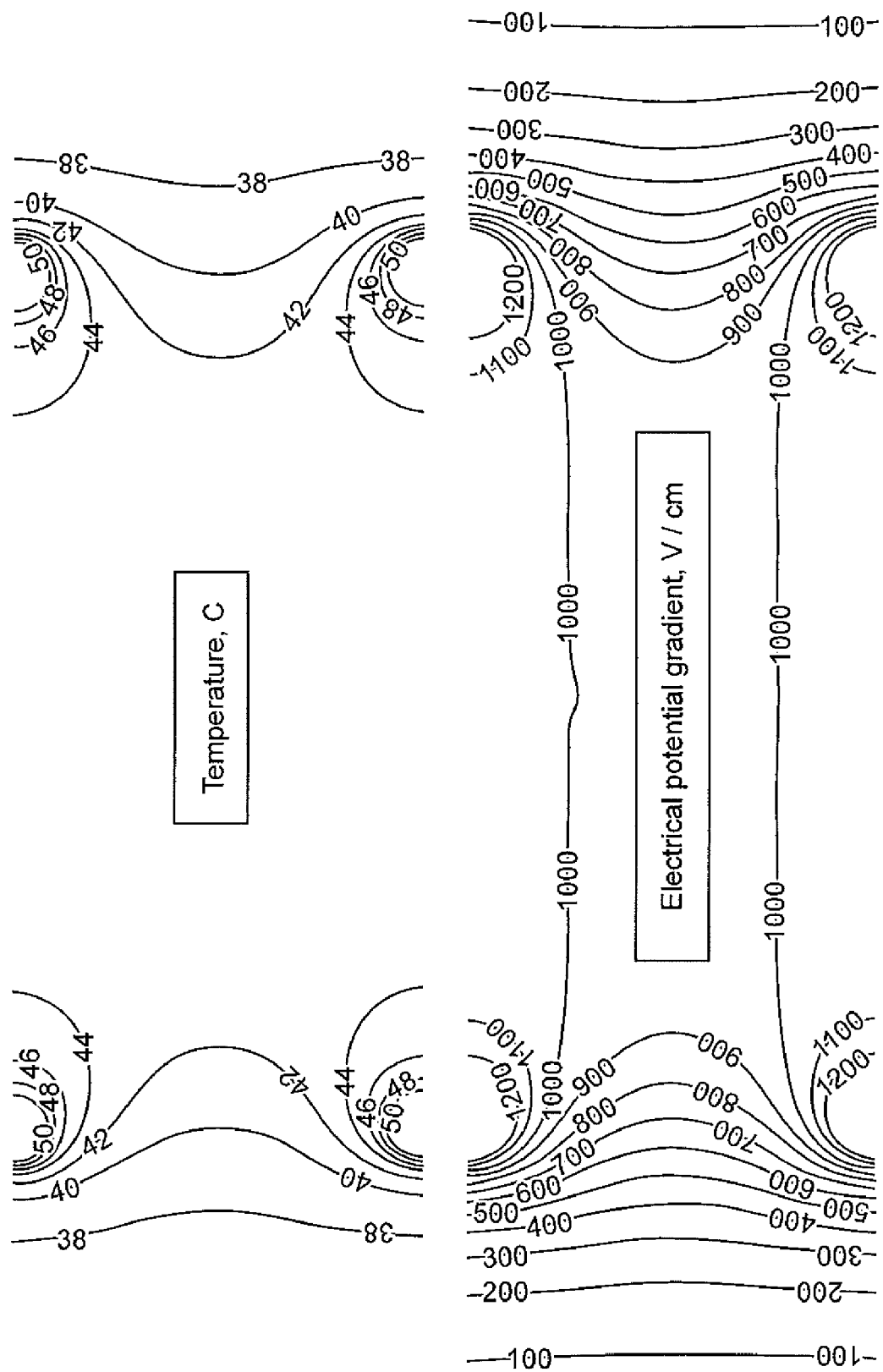
FIG. 12 shows lines for calculated temperature distribution (C), upper panel, and electrical potential gradient (electroporation gradient) (V/cm), lower panel, for the in vivo experiment.
Figure 13:
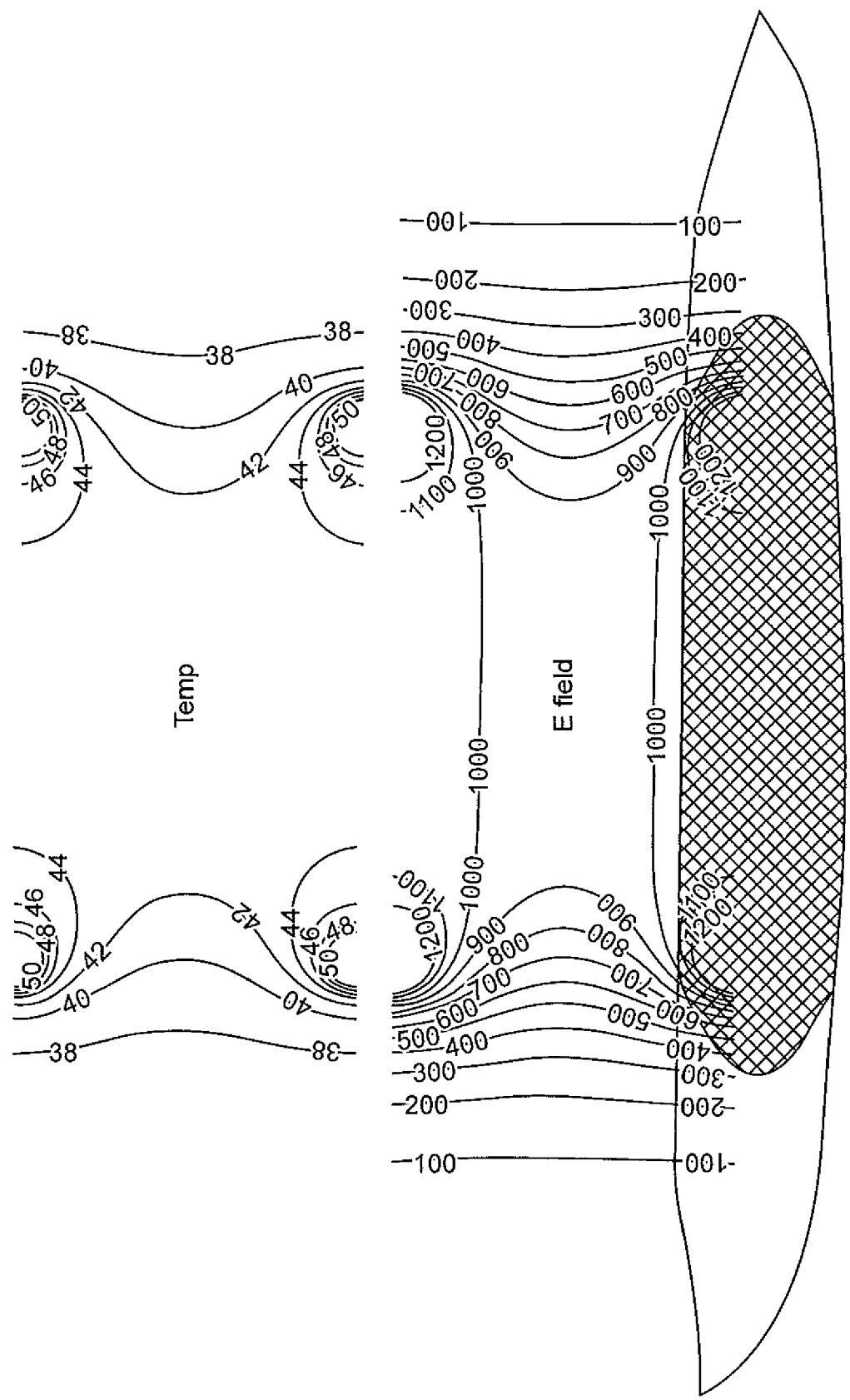
FIG. 13 combines FIGS. 11 and 12 to show a comparison between the extent of tissue necrosis (dark area) and the temperature and voltage gradient distribution in the electroporated tissue. It is evident that most of the dark area was at a temperature of about 42° C. following the 40 milliseconds electroporation pulse. The edge of the dark area seems to correspond to the 300 V/cm electroporation gradient line.

The goal of this experiment was to verify the ability of irreversible electroporation pulses to produce substantial tissue ablation in the non-thermal regime. To this end we have performed experiments on the liver of Spraque-Dawley male rats (250 g to 350 g) under an approved animal use and care protocol. After the animals were anesthetized by injection of Nembutal Sodium Solution (50 mg/ml Pentobarbital) the liver was exposed via a midline incisions and one lobed clamped between two cylindrical electrodes of Ag/AgCl, with a diameter of 10 mm (In Vivo Metric, Healdsburg, Calif.). The electrodes had their flat surface parallel; they were concentric and the liver between the electrodes was compressed so that the lobes were separated by 4 mm. A schematic of the electrodes and the liver is shown in FIG. 9. The liver was exposed to a single electroporation pulse of 40 milliseconds. One electrode was set to 400 V and the other grounded. The rest of the liver was not in contact with any media and therefore is considered electrically insulated. After electroporation the rat was maintained under controlled anesthesia for three hours. Following exsanguination the liver was flushed with physiological saline under pressure and fixed by perfusion with formaldehyde. The liver was resected through the center of the electroporated region and analyzed by histology. FIGS. 10 and 11 show the appearance of the liver. Histology has determined that the dark area corresponds to the region of tissue necrosis. The electrical field in the electroporated liver and the temperature distribution were calculated using the equations in Example 1, subject to one electrode at a voltage of 400V and the other grounded, for 40 milliseconds. The liver was modeled as an infinite slab of 4 mm thickness, with concentric cylindrical electrodes (see FIG. 9). The results are shown in FIG. 12. FIG. 12 shows lines of constant voltage gradients (V/cm) and lines of constant temperature. It is evident that in the majority of the electroporated tissue the temperature is about 42° C. immediately after the pulse. The highest temperature occurs near the edge of the cylindrical electrodes, where it is about 50° C. FIG. 13 was obtained by bringing together FIGS. 11 and 12. Superimposing the calculated results on the histological measurements reveals that the dark (necrotic) area margin corresponds to electroporation parameters of about 300 V/cm. The results demonstrate that irreversible electroporation can induce substantial tissue necrosis without the need for chemical additives as in electrochemotherapy and without a thermal effect.

The results obtained by disrupting blood flow to a given area are dramatically shown in FIG. 14 which is a photo of a micrograph. This micrograph is from the interface between irreversible electroporated liver and normal liver. The left hand side shows normal hepatocytes with clear nucleus and nuclei. The photo shows well defined cell membranes and clean (flushed) sinusoids. The right hand side of FIG. 14 shows condensed nuclei, no evidence of cell membrane, and an expanded cell border with no evidence of sinusoids. The disintegrated red blood cells shown in FIG. 14 are in what could have been the spaces of the sinusoids. Flushing is not believed to have had an effect on the results obtained on the right-hand side of FIG. 14.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of disrupting capillary blood flow and facilitating the permeation of an agent into a target area of tissue, comprising the steps of:
   (a) identifying a target tissue comprised of capillaries;
   (b) placing a first electrode and a second electrode such that capillaries of the target tissue are positioned between the first and second electrodes;
   (c) administering an agent to a vessel at a point upstream of the capillaries of the target tissue; and
   (d) after administering the agent, applying electrical pulses between the first and second electrode to intentionally cause irreversible electroporation of cells of the capillaries of the target tissue, and disrupt blood flow through the capillaries of the target tissue, thereby trapping the agent in the capillaries and facilitating the permeation of the agent into cells of the target tissue.

2. The method of claim 1, wherein the administered agent is a chemotherapeutic agent and the capillaries are blood vessels having a diameter of from 1 μm to 10 μm.

3. The method of claim 2, further comprising:
   (e) allowing the cells of the target tissue to be killed by the chemotherapeutic agent and thereafter be removed by internal systems of an organism comprised of the target tissue.

4. The method of claim 1, wherein the capillaries are blood vessels having a diameter of from 4 μm to 7 μm and wherein the target tissue is chosen from a cancerous tumor, a benign tumor and a uterine fibroid.

5. The method of claim 1, wherein from 1 to 100 electrical pulses are applied for a duration in a range of from about 5 microseconds to about 62 seconds.

6. The method of claim 1, wherein the electrical pulses are applied for a period of 100 microseconds, ±10 microseconds and wherein from 2 to 50 pulses are applied.

7. The method of claim 1, wherein 5 to 25 electrical pulses of 100 microseconds each in duration are applied and wherein the electrical pulses produce a voltage gradient in a range of from 50 volt/cm to 8000 volt/cm.

8. The method of claim 1, wherein the first electrode is placed at about 5 mm to 10 cm from the second electrode and are positioned upstream of the target tissue in a direction of blood flow toward the target tissue and wherein the first electrode and second electrode are circular in shape and wherein the first electrode and the second electrode each have a surface area of about 1 square centimeter.

9. A method of claim 1, further comprising:
   (f) adjusting applied voltage, length of pulses, and number of pulse to obtain capillary blood flow disruption in the tissue of interest thereby minimizing damage to surrounding tissue.

10. A method of treating cancer, comprising:
    (a) identifying a grouping of biological cells in a tissue of a living mammal as being target tissue cancer cells;
    (b) infusing a chemotherapeutic agent into a bed of capillaries immediately upstream of the target tissue cancer cells; and
    (c) applying an electrical current when the agent reaches the target tissue cancer cells, to intentionally cause irreversible electroporation of cells of the capillaries of the target tissue cancer cells, and to disrupt capillary blood flow so as to trap the chemotherapeutic agent in capillaries of the target tissue cancer cells.

11. The method of claim 10, further comprising:
    (d) continuously detecting a ratio of electric current through the cells to voltage across the cells as an indication of degree of electroporation of the biological cells; and
    (e) adjusting a determined magnitude of the applied voltage in accordance with changes in detected magnitude of the current-to-voltage ratio to achieve a disruption of capillary blood flow and permeation of the chemotherapeutic agent into capillary endothelial cells that vascularize the grouping of cells identified as being cancer cells.

12. The method of claim 11, wherein step (d) comprises continuously detecting the current-to-voltage ratio in an indication of onset of electroporation of biological cells, and step (e) comprises adjusting the duration of the applied voltage in accordance with continuously detected current-to-voltage ratio to achieve disruption of capillary blood flow to the grouping of cells identified as being cancer cells.

13. The method of claim 12, wherein the current-to-voltage ratio is an indication of degree of electroporation averaged over the cells identified as cancer cells, and of the disruption of capillary blood flow to the cancer cells.

14. The method of claim 10, wherein (c) is carried out by applying current between two microelectrodes positioned on either side of a group of capillaries providing blood to the cancer cells and wherein the cancer cells are in a human and the current is in pulses of 100 microseconds ± about 10 microseconds at a voltage gradient in a range of from about 50 volt/cm to about 8000 volt/cm.

15. A method of enhancing the delivery of an agent into a target area of tissue, comprising the steps of:
 (a) identifying an area of tissue of interest comprised of capillaries as target tissue;
 (b) placing a first electrode and a second electrode such that capillaries of the identified tissue of interest are positioned between the first and second electrodes;
 (c) administering an agent at a point in a vessel upstream of the capillaries; and
 (d) after administering the agent, applying electrical pulses between the first and second electrode to intentionally cause irreversible electroporation of cells of the capillaries of the target tissue, and to disrupt flow through the capillaries of the target tissue.

16. The method of claim 15, wherein the agent is a medical imaging agent.

17. The method of claim 15, wherein the capillaries have a diameter of less than 8 μm.

18. The method of claim 15, wherein the capillaries have a diameter in a range of from 4 μm to 7 μm and from 1 to 100 pulses are applied with each pulse being applied for a duration of from 5 microseconds to 62 seconds at a voltage of from 50 volts/cm to 8,000 volts/cm while maintaining target tissue temperature at 50° C. or less.

* * * * *